(12) United States Patent
Stevens et al.

(10) Patent No.: US 11,370,843 B2
(45) Date of Patent: Jun. 28, 2022

(54) HIGH AFFINITY ANTIBODIES TO HUMAN IL-6 RECEPTOR

(71) Applicant: REGENERON PHARMACEUTICALS, INC., Tarrytown, NY (US)

(72) Inventors: Sean Stevens, Del Mar, CA (US); Tammy T. Huang, Cross River, NY (US); Joel H. Martin, Putnam Valley, NY (US); Jeanette L. Fairhurst, White Plains, NY (US); Ashique Rafique, Yonkers, NY (US); Eric Smith, New York, NY (US); Kevin J. Pobursky, Warren, MI (US); Nicholas J. Papadopoulos, LaGrangeville, NY (US); James P. Fandl, LaGrangeville, NY (US); Gang Chen, Yorktown Heights, NY (US); Margaret Karow, Santa Rosa Valley, CA (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 16/774,945

(22) Filed: Jan. 28, 2020

(65) Prior Publication Data

US 2021/0009698 A1 Jan. 14, 2021

Related U.S. Application Data

(60) Continuation of application No. 16/119,695, filed on Aug. 31, 2018, now Pat. No. 10,584,173, which is a continuation of application No. 15/865,508, filed on Jan. 9, 2018, now abandoned, which is a continuation of application No. 15/136,152, filed on Apr. 22, 2016, now Pat. No. 9,884,916, which is a continuation of application No. 14/206,259, filed on Mar. 12, 2014, now abandoned, which is a continuation of application No. 13/450,011, filed on Apr. 18, 2012, now abandoned, which is a division of application No. 13/230,081, filed on Sep. 12, 2011, now Pat. No. 8,183,014, which is a continuation of application No. 12/501,657, filed on Jul. 13, 2009, now Pat. No. 8,043,617, which is a division of application No. 11/809,482, filed on Jun. 1, 2007, now Pat. No. 7,582,298.

(60) Provisional application No. 60/843,232, filed on Sep. 8, 2006, provisional application No. 60/810,664, filed on Jun. 2, 2006.

(51) Int. Cl.
*C07K 16/28* (2006.01)
*C12N 15/12* (2006.01)
*A61K 39/00* (2006.01)

(52) U.S. Cl.
CPC .... *C07K 16/2866* (2013.01); *A61K 2039/505* (2013.01); *C07K 2317/14* (2013.01); *C07K 2317/21* (2013.01); *C07K 2317/56* (2013.01); *C07K 2317/565* (2013.01); *C07K 2317/76* (2013.01); *C07K 2317/92* (2013.01)

(58) Field of Classification Search
CPC .......................... C07K 16/2866; C12N 15/00
See application file for complete search history.

(56) References Cited

U.S. PATENT DOCUMENTS

| | | |
|---|---|---|
| 5,480,796 A | 1/1996 | Kishimoto |
| 5,670,373 A | 9/1997 | Kishimoto |
| 5,723,120 A | 3/1998 | Brackenhoff et al. |
| 5,795,965 A | 8/1998 | Tsuchiya |
| 5,817,790 A | 10/1998 | Tsuchiya |
| 5,888,510 A | 3/1999 | Kishimoto |
| 5,888,511 A | 3/1999 | Skurkovich et al. |
| 6,086,874 A | 7/2000 | Yoshida et al. |
| 6,261,560 B1 | 7/2001 | Tsujinaka et al. |
| 6,410,691 B1 | 6/2002 | Kishimoto |
| 6,632,927 B2 | 10/2003 | Adair |
| 6,692,742 B1 | 2/2004 | Nakamura et al. |
| 6,723,319 B1 | 4/2004 | Ito |
| 7,320,792 B2 | 1/2008 | Ito et al. |
| 7,479,543 B2 | 1/2009 | Tsuchiya et al. |
| 7,582,298 B2 | 9/2009 | Stevens |
| 8,192,741 B2 | 6/2012 | Radin |
| 2002/0187150 A1 | 12/2002 | Mihara et al. |
| 2004/0071706 A1 | 4/2004 | Ito et al. |
| 2004/0115197 A1 | 6/2004 | Yoshizaki et al. |
| 2004/0219156 A1 | 11/2004 | Goldenberg et al. |
| 2005/0142635 A1 | 6/2005 | Tsuchiya et al. |

(Continued)

FOREIGN PATENT DOCUMENTS

| EP | 0 628 639 | 12/1994 |
|---|---|---|
| EP | 0 409 607 | 10/1996 |

(Continued)

OTHER PUBLICATIONS

Amit et al., "Three-Dimensional Structure of an Antigen-Antibody Complex at 2.8 a Resolution" Science (Aug. 1986) 233:747-753.

(Continued)

*Primary Examiner* — Prema M Mertz
(74) *Attorney, Agent, or Firm* — Karl Bozicevic; Bozicevic, Field & Francis LLP

(57) ABSTRACT

A human antibody or an antigen-binding fragment which binds human IL-6 receptor (hIL-6R) with a $K_D$ of about 500 pM or less and blocks IL-6 activity with an $IC_{50}$ of 200 pM or less, is provided. In preferred embodiments, the antibody the antibody or antigen-binding fragment binds hIL-6R with an affinity at least 2-fold higher relative to its binding monkey IL-6R.

15 Claims, No Drawings

Specification includes a Sequence Listing.

(56) References Cited

U.S. PATENT DOCUMENTS

| | | |
|---|---|---|
| 2005/0238644 A1 | 10/2005 | Mihara et al. |
| 2006/0078531 A1 | 4/2006 | Sota |
| 2006/0078532 A1 | 4/2006 | Omoigui |
| 2006/0078533 A1 | 4/2006 | Omoigui |
| 2006/0177436 A1 | 8/2006 | Ghilardi et al. |
| 2006/0251653 A1 | 11/2006 | Okuda et al. |
| 2006/0275294 A1 | 12/2006 | Omoigui |
| 2006/0292147 A1 | 12/2006 | Yoshizaki et al. |
| 2007/0036785 A1 | 2/2007 | Kishimoto et al. |
| 2007/0036788 A1 | 2/2007 | Sheriff et al. |
| 2007/0098714 A1 | 5/2007 | Nishimoto et al. |
| 2007/0148169 A1 | 6/2007 | Yoshizaki et al. |
| 2007/0280945 A1 | 12/2007 | Stevens et al. |
| 2008/0124325 A1 | 5/2008 | Ito et al. |
| 2008/0145367 A1 | 6/2008 | Bove et al. |

FOREIGN PATENT DOCUMENTS

| | | |
|---|---|---|
| EP | 0 783 893 | 7/1997 |
| EP | 0 800 829 | 10/1997 |
| EP | 0 811 384 | 12/1997 |
| EP | 0 628 639 | 6/1999 |
| EP | 0 923 941 | 6/1999 |
| EP | 1 004 315 | 5/2000 |
| EP | 1 074 268 | 2/2001 |
| EP | 1 108 435 | 6/2001 |
| EP | 1 314 437 | 5/2003 |
| EP | 1 327 681 | 7/2003 |
| EP | 1 334 731 | 8/2003 |
| EP | 1 475 100 | 11/2004 |
| EP | 1 475 101 | 11/2004 |
| EP | 0 413 908 | 8/2005 |
| EP | 0 923 941 | 5/2006 |
| EP | 0 811 384 | 6/2006 |
| EP | 1 108 435 | 1/2007 |
| EP | 1 810 980 | 7/2007 |
| EP | 1 074 268 | 1/2008 |
| EP | 1 334 731 | 2/2008 |
| EP | 1 004 315 | 5/2008 |
| FR | 2694767 | 2/1994 |
| WO | WO 95/09873 | 4/1995 |
| WO | WO 2004/096273 | 11/2004 |
| WO | WO 2005/028514 | 3/2005 |
| WO | WO 2007/143168 | 12/2007 |
| WO | WO 2008/020079 | 2/2008 |
| WO | WO 2008/049897 | 5/2008 |
| WO | WO 2008/145142 | 12/2008 |
| WO | WO 2009/095489 | 8/2009 |
| WO | WO 2009/109584 | 9/2009 |

OTHER PUBLICATIONS

Hirata et al., "Characterization of IL-6 Receptor Expression By Monoclonal and Polyclonal Antibodies" J. Immunol. (1989) 143(9):2900-2906.

Lederman et al. "A Single Amino Acid Substitution in a Common African Allele of the CD4 Molecule Ablates Binding of the Monoclonal Antibody, OKT4" Molecular Immunology (1991) 28(11):1171-1181.

Li et al. "Temporal associations between interleukin 22 and the extracellular domains of IL-22R and IL-10R2" International Immunology (2004) 4:693-708.

Mihara et al., 2005, Tocilizumab inhibits signal transduction mediated by both MIL-6R and sIL-6R, but not by the receptors of other members of IL-6 cyotkine family, International Immunopharmacoloav 5:1731-1740.

Panka et al., "Variable Region Framework Differences Result in Decreased or Increased Affinity of Variant Anti-Digoxin Antibodies" Proc. Natl. Acad. Sci. USA (May 1988) 85:3080-3084.

Paul-Ple Izer, 2006, Tocilizumab: Blockade of interleukin-6 signaling pathway as a therapeautic strategy for inflammatory disorders, Drugs of Today 42(9):559-576.

Presta, Leonard G., "Engineering of therapeutic antibodies to minimize immunogenicity and optimize function" Advanced Drug Delivery Reviews (2006) 58:640-656.

Rudikoff et al., "Single Amino Acid Substitution Altering Antigen-Binding Specificity" Proc. Natl. Acad. Sci. USA (Mar. 1982) 79:1979-1983.

Uchiyama et al., "Tocilizumab, a Humanized Anti-interleukin-6 Receptor Antibody, Ameliorates Joing Swelling in Established Monkey Collagen-Induced Arthritis" Biol. Pharm. Bull. (2008) 31(6):1159-1163.

SEQUENCE LISTING

<160> NUMBER OF SEQ ID NOS: 251

<210> SEQ ID NO 1
<211> LENGTH: 358
<212> TYPE: PRT
<213> ORGANISM: Homo sapiens

<400> SEQUENCE: 1

Met Val Ala Val Gly Cys Ala Leu Leu Ala Ala Leu Leu Ala Ala Pro
1               5                   10                  15

Gly Ala Ala Leu Ala Pro Arg Arg Cys Pro Ala Gln Glu Val Ala Arg
            20                  25                  30

Gly Val Leu Thr Ser Leu Pro Gly Asp Ser Val Thr Leu Thr Cys Pro
        35                  40                  45

Gly Val Glu Pro Glu Asp Asn Ala Thr Val His Trp Val Leu Arg Lys
    50                  55                  60

Pro Ala Ala Gly Ser His Pro Ser Arg Trp Ala Gly Met Gly Arg Arg
65                  70                  75                  80

```
Leu Leu Leu Arg Ser Val Gln Leu His Asp Ser Gly Asn Tyr Ser Cys
                85                  90                  95
Tyr Arg Ala Gly Arg Pro Ala Gly Thr Val His Leu Val Asp Val
            100                 105                 110
Pro Pro Glu Glu Pro Gln Leu Ser Cys Phe Arg Lys Ser Pro Leu Ser
            115                 120                 125
Asn Val Val Cys Glu Trp Gly Pro Arg Ser Thr Pro Ser Leu Thr Thr
        130                 135                 140
Lys Ala Val Leu Leu Val Arg Lys Phe Gln Asn Ser Pro Ala Glu Asp
145                 150                 155                 160
Phe Gln Glu Pro Cys Gln Tyr Ser Gln Glu Ser Gln Lys Phe Ser Cys
                165                 170                 175
Gln Leu Ala Val Pro Glu Gly Asp Ser Ser Phe Tyr Ile Val Ser Met
            180                 185                 190
Cys Val Ala Ser Ser Val Gly Ser Lys Phe Ser Lys Thr Gln Thr Phe
            195                 200                 205
Gln Gly Cys Gly Ile Leu Gln Pro Asp Pro Pro Ala Asn Ile Thr Val
        210                 215                 220
Thr Ala Val Ala Arg Asn Pro Arg Trp Leu Ser Val Thr Trp Gln Asp
225                 230                 235                 240
Pro His Ser Trp Asn Ser Ser Phe Tyr Arg Leu Arg Phe Glu Leu Arg
                245                 250                 255
Tyr Arg Ala Glu Arg Ser Lys Thr Phe Thr Thr Trp Met Val Lys Asp
            260                 265                 270
Leu Gln His His Cys Val Ile His Asp Ala Trp Ser Gly Leu Arg His
            275                 280                 285
Val Val Gln Leu Arg Ala Gln Glu Glu Phe Gly Gln Gly Glu Trp Ser
        290                 295                 300
Glu Trp Ser Pro Glu Ala Met Gly Thr Pro Trp Thr Glu Ser Arg Ser
305                 310                 315                 320
Pro Pro Ala Glu Asn Glu Val Ser Thr Pro Met Gln Ala Leu Thr Thr
                325                 330                 335
Asn Lys Asp Asp Asp Asn Ile Leu Phe Arg Asp Ser Ala Asn Ala Thr
            340                 345                 350
Ser Leu Pro Val Gln Asp
        355

<210> SEQ ID NO 2
<211> LENGTH: 379
<212> TYPE: DNA
<213> ORGANISM: Artificial Sequence
<220> FEATURE:
<223> OTHER INFORMATION: Synthetic

<400> SEQUENCE: 2
gaagtgcagc tggtggagtc tgggggaaac ttggtacagc ctggcaggtc cctgagactc      60
tcctgtgcag cctctggatt catctttgat gattatgcca tgcactgggt ccggcaagct     120
ccagggaagg gcctggagtg ggtctcaggt attagttgga atagtggtag cataggctat     180
gcggactctg tgaagggccg attcaccatc tccagagaca cgccaagaa ctccctgtat      240 ctgcaaatga acagtctgag agctgaggac acggccttgt attactgtgc aaaagatgga     300
ggcagcagct ggttaccgtt cgtctactac tacggtatgg acgtctgggg ccaagggacc     360
acggtcaccg tctcgtcag                                                  379
```

<210> SEQ ID NO 3
<211> LENGTH: 126
<212> TYPE: PRT
<213> ORGANISM: Artificial Sequence
<220> FEATURE:
<223> OTHER INFORMATION: Synthetic

<400> SEQUENCE: 3

```
Glu Val Gln Leu Val Glu Ser Gly Gly Asn Leu Val Gln Pro Gly Arg
1               5                   10                  15

Ser Leu Arg Leu Ser Cys Ala Ala Ser Gly Phe Ile Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Gly Gly Ser Ser Trp Leu Pro Phe Val Tyr Tyr Tyr Gly
            100                 105                 110

Met Asp Val Trp Gly Gln Gly Thr Thr Val Thr Val Ser Ser
        115                 120                 125
```

<210> SEQ ID NO 4
<211> LENGTH: 24
<212> TYPE: DNA
<213> ORGANISM: Artificial Sequence
<220> FEATURE:
<223> OTHER INFORMATION: Synthetic

<400> SEQUENCE: 4
ggattcatct ttgatgatta tgcc                                      24

<210> SEQ ID NO 5
<211> LENGTH: 8
<212> TYPE: PRT
<213> ORGANISM: Artificial Sequence
<220> FEATURE:
<223> OTHER INFORMATION: Synthetic

<400> SEQUENCE: 5

```
Gly Phe Ile Phe Asp Asp Tyr Ala
1               5
```

<210> SEQ ID NO 6
<211> LENGTH: 24
<212> TYPE: DNA
<213> ORGANISM: Artificial Sequence
<220> FEATURE:
<223> OTHER INFORMATION: Synthetic

<400> SEQUENCE: 6
attagttgga atagtggtag cata                                      24

<210> SEQ ID NO 7
<211> LENGTH: 8
<212> TYPE: PRT
<213> ORGANISM: Artificial Sequence
<220> FEATURE:
<223> OTHER INFORMATION: Synthetic

<400> SEQUENCE: 7

Ile Ser Trp Asn Ser Gly Ser Ile
1               5

<210> SEQ ID NO 8
<211> LENGTH: 57
<212> TYPE: DNA
<213> ORGANISM: Artificial Sequence
<220> FEATURE:
<223> OTHER INFORMATION: Synthetic

<400> SEQUENCE: 8
gcaaaagatg gaggcagcag ctggttaccg ttcgtctact actacggtat ggacgtc      57

<210> SEQ ID NO 9
<211> LENGTH: 19
<212> TYPE: PRT
<213> ORGANISM: Artificial Sequence
<220> FEATURE:
<223> OTHER INFORMATION: Synthetic

<400> SEQUENCE: 9

Ala Lys Asp Gly Gly Ser Ser Trp Leu Pro Phe Val Tyr Tyr Gly
1               5                   10                  15

Met Asp Val

<210> SEQ ID NO 10
<211> LENGTH: 325
<212> TYPE: DNA
<213> ORGANISM: Artificial Sequence
<220> FEATURE:
<223> OTHER INFORMATION: Synthetic

<400> SEQUENCE: 10
gaaatagtga tgacgcagtc tccagccacc ctgtctgtgt ctcccgggga aagagccacc      60
ctctcctgca gggccagtca gagtattagc agcaactttg cctggtacca gcagaaacct     120
ggccaggctc ccaggctcct catctatggt gcatccacca gggccactgg tatcccagcc     180
aggttcagtg gcagtgggtc tgggacagac ttcactctca ccatcagcag cctgcagtct     240
gaagattttg cagtttatta ctgtcagcag tatagtagct ggcctccgta cactttggc      300 caggggacca agctggagat caaac                                           325

<210> SEQ ID NO 11
<211> LENGTH: 108
<212> TYPE: PRT
<213> ORGANISM: Artificial Sequence
<220> FEATURE:
<223> OTHER INFORMATION: Synthetic

<400> SEQUENCE: 11

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Ser Asn
            20                  25                  30

Phe Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Asp Phe Thr Leu Thr Ile Ser Ser Leu Gln Ser
65                  70                  75                  80

```
Glu Asp Phe Ala Val Tyr Tyr Cys Gln Gln Tyr Ser Ser Trp Pro Pro
                85                  90                  95
Tyr Thr Phe Gly Gln Gly Thr Lys Leu Glu Ile Lys
            100                 105
```

<210> SEQ ID NO 12
<211> LENGTH: 18
<212> TYPE: DNA
<213> ORGANISM: Artificial Sequence
<220> FEATURE:
<223> OTHER INFORMATION: Synthetic

<400> SEQUENCE: 12
cagagtatta gcagcaac                                              18

<210> SEQ ID NO 13
<211> LENGTH: 6
<212> TYPE: PRT
<213> ORGANISM: Artificial Sequence
<220> FEATURE:
<223> OTHER INFORMATION: Synthetic

<400> SEQUENCE: 13

```
Gln Ser Ile Ser Ser Asn
1               5
```

<210> SEQ ID NO 14
<211> LENGTH: 9
<212> TYPE: DNA
<213> ORGANISM: Artificial Sequence
<220> FEATURE:
<223> OTHER INFORMATION: Synthetic

<400> SEQUENCE: 14 ggtgcatcc                                                         9

<210> SEQ ID NO 15
<211> LENGTH: 3
<212> TYPE: PRT
<213> ORGANISM: Artificial Sequence
<220> FEATURE:
<223> OTHER INFORMATION: Synthetic

<400> SEQUENCE: 15

```
Gly Ala Ser
1
```

<210> SEQ ID NO 16
<211> LENGTH: 30
<212> TYPE: DNA
<213> ORGANISM: Artificial Sequence
<220> FEATURE:
<223> OTHER INFORMATION: Synthetic

<400> SEQUENCE: 16
cagcagtata gtagctggcc tccgtacact                                 30

<210> SEQ ID NO 17
<211> LENGTH: 10
<212> TYPE: PRT
<213> ORGANISM: Artificial Sequence
<220> FEATURE:
<223> OTHER INFORMATION: Synthetic

<400> SEQUENCE: 17

```
Gln Gln Tyr Ser Ser Trp Pro Pro Tyr Thr
```

<210> SEQ ID NO 18
<211> LENGTH: 349
<212> TYPE: DNA
<213> ORGANISM: Artificial Sequence
<220> FEATURE:
<223> OTHER INFORMATION: Synthetic

<400> SEQUENCE: 18

```
gaagtgcagc tggtggagtc tgggggaggc ttggttcagc ctggcaggtc cctgagactc     60
tcctgtgcag cctctagatt tacctttgat gattatgcca tgcactgggt ccggcaagct    120
ccagggaagg gcctggagtg ggtctcaggt attagttgga atagtggtag aataggttat    180
gcggactctg tgaagggccg attcaccatc tccagagaca cgccgagaa ctccctcttt    240
ctgcaaatga acggtctgag agcagaggac acggccttgt attactgtgc aaaaggccga    300
gattcttttg atatctgggg ccaagggaca atggtcaccg tctcttcag                349
```

<210> SEQ ID NO 19
<211> LENGTH: 116
<212> TYPE: PRT
<213> ORGANISM: Artificial Sequence
<220> FEATURE:
<223> OTHER INFORMATION: Synthetic

<400> SEQUENCE: 19

```
Glu Val Gln Leu Val Glu Ser Gly Gly Gly Leu Val Gln Pro Gly Arg
1               5                   10                  15

Ser Leu Arg Leu Ser Cys Ala Ala Ser Arg Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Arg Ile Gly Tyr Ala Asp Ser Val
    50                  55                  60

Lys Gly Arg Phe Thr Ile Ser Arg Asp Asn Ala Glu Asn Ser Leu Phe
65                  70                  75                  80

Leu Gln Met Asn Gly Leu Arg Ala Glu Asp Thr Ala Leu Tyr Tyr Cys
                85                  90                  95

Ala Lys Gly Arg Asp Ser Phe Asp Ile Trp Gly Gln Gly Thr Met Val
            100                 105                 110

Thr Val Ser Ser
        115
```

<210> SEQ ID NO 20
<211> LENGTH: 24
<212> TYPE: DNA
<213> ORGANISM: Artificial Sequence
<220> FEATURE:
<223> OTHER INFORMATION: Synthetic

<400> SEQUENCE: 20

```
agatttacct ttgatgatta tgcc                                             24
```

<210> SEQ ID NO 21
<211> LENGTH: 8
<212> TYPE: PRT
<213> ORGANISM: Artificial Sequence
<220> FEATURE:
<223> OTHER INFORMATION: Synthetic

<400> SEQUENCE: 21

Arg Phe Thr Phe Asp Asp Tyr Ala
1               5

<210> SEQ ID NO 22
<211> LENGTH: 24
<212> TYPE: DNA
<213> ORGANISM: Artificial Sequence
<220> FEATURE:
<223> OTHER INFORMATION: Synthetic

<400> SEQUENCE: 22
attagttgga atagtggtag aata                                          24

<210> SEQ ID NO 23
<211> LENGTH: 8
<212> TYPE: PRT
<213> ORGANISM: Artificial Sequence
<220> FEATURE:
<223> OTHER INFORMATION: Synthetic

<400> SEQUENCE: 23

Ile Ser Trp Asn Ser Gly Arg Ile
1               5

<210> SEQ ID NO 24
<211> LENGTH: 27
<212> TYPE: DNA
<213> ORGANISM: Artificial Sequence
<220> FEATURE:
<223> OTHER INFORMATION: Synthetic

<400> SEQUENCE: 24
gcaaaaggcc gagattcttt tgatatc                                       27

<210> SEQ ID NO 25
<211> LENGTH: 9
<212> TYPE: PRT
<213> ORGANISM: Artificial Sequence
<220> FEATURE:
<223> OTHER INFORMATION: Synthetic

<400> SEQUENCE: 25

Ala Lys Gly Arg Asp Ser Phe Asp Ile
1               5

<210> SEQ ID NO 26
<211> LENGTH: 322
<212> TYPE: DNA
<213> ORGANISM: Artificial Sequence
<220> FEATURE:
<223> OTHER INFORMATION: Synthetic

<400> SEQUENCE: 26
gacatccaga tgacccagtc tccatcttcc gtgtctgcat ctgtaggaga cagagtcacc    60
atcacttgtc gggcgagtca gggtattagc agctggttag cctggtatca gcagaaacca   120
gggaaagccc ctaagctcct gatctatggt gcatccagtt tggaaagtgg ggtcccatca   180
aggttcagcg gcagtggatc tgggacagat tcactctca ccatcagcag cctgcagcct    240
gaagattttg caagttatta ttgtcaacag gctaacagtt tcccgtacac ttttggccag   300
gggaccaagc tggagatcaa ac                                            322

<210> SEQ ID NO 27
<211> LENGTH: 107

```
<212> TYPE: PRT
<213> ORGANISM: Artificial Sequence
<220> FEATURE:
<223> OTHER INFORMATION: Synthetic

<400> SEQUENCE: 27

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ser Tyr Tyr Cys Gln Gln Ala Asn Ser Phe Pro Tyr
                85                  90                  95

Thr Phe Gly Gln Gly Thr Lys Leu Glu Ile Lys
            100                 105

<210> SEQ ID NO 28
<211> LENGTH: 18
<212> TYPE: DNA
<213> ORGANISM: Artificial Sequence
<220> FEATURE:
<223> OTHER INFORMATION: Synthetic

<400> SEQUENCE: 28
cagggtatta gcagctgg                                                   18

<210> SEQ ID NO 29
<211> LENGTH: 6
<212> TYPE: PRT
<213> ORGANISM: Artificial Sequence
<220> FEATURE:
<223> OTHER INFORMATION: Synthetic

<400> SEQUENCE: 29

Gln Gly Ile Ser Ser Trp
1               5

<210> SEQ ID NO 30
<211> LENGTH: 9
<212> TYPE: DNA
<213> ORGANISM: Artificial Sequence
<220> FEATURE:
<223> OTHER INFORMATION: Synthetic

<400> SEQUENCE: 30 ggtgcatcc                                                              9

<210> SEQ ID NO 31
<211> LENGTH: 3
<212> TYPE: PRT
<213> ORGANISM: Artificial Sequence
<220> FEATURE:
<223> OTHER INFORMATION: Synthetic

<400> SEQUENCE: 31

Gly Ala Ser
1
```

<210> SEQ ID NO 32
<211> LENGTH: 27
<212> TYPE: DNA
<213> ORGANISM: Artificial Sequence
<220> FEATURE:
<223> OTHER INFORMATION: Synthetic

<400> SEQUENCE: 32
caacaggcta acagtttccc gtacact                                         27

<210> SEQ ID NO 33
<211> LENGTH: 9
<212> TYPE: PRT
<213> ORGANISM: Artificial Sequence
<220> FEATURE:
<223> OTHER INFORMATION: Synthetic

<400> SEQUENCE: 33

Gln Gln Ala Asn Ser Phe Pro Tyr Thr
1               5

<210> SEQ ID NO 34
<211> LENGTH: 370
<212> TYPE: DNA
<213> ORGANISM: Artificial Sequence
<220> FEATURE:
<223> OTHER INFORMATION: Synthetic

<400> SEQUENCE: 34
caggttcagc tggtgcagtc tggagctgag ctgaagaagc ctggggcctc agtgaaggtc      60
tcctgcaagg cttctggtta cactttttacc cattatggta tcagctgggt gcgacaggcc     120
cctggacaag gcttgagtg gatgggatgg atcagcgctt acaatgatga cacaaactat      180
gcacagaagt tccagggag agtcaccatg accacagaca catccacgag cacagcctac     240
atggagctga ggagcctgag atctgacgac acggccgttt attactgtgc gagagaagcg     300
cagctcgtcc tctactacta ctacggtatg gacgtctggg gccaagggac cacggtcacc     360
gtctcctcag                                                             370

<210> SEQ ID NO 35
<211> LENGTH: 123
<212> TYPE: PRT
<213> ORGANISM: Artificial Sequence
<220> FEATURE:
<223> OTHER INFORMATION: Synthetic

<400> SEQUENCE: 35

Gln Val Gln Leu Val Gln Ser Gly Ala Glu Leu Lys Lys Pro Gly Ala
1               5                   10                  15
Ser Val Lys Val Ser Cys Lys Ala Ser Gly Tyr Thr Phe Thr His Tyr
            20                  25                  30
Gly Ile Ser Trp Val Arg Gln Ala Pro Gly Gln Gly Leu Glu Trp Met
        35                  40                  45
Gly Trp Ile Ser Ala Tyr Asn Asp Asp Thr Asn Tyr Ala Gln Lys Phe
    50                  55                  60
Gln Gly Arg Val Thr Met Thr Thr Asp Thr Ser Thr Ser Thr Ala Tyr
65                  70                  75                  80
Met Glu Leu Arg Ser Leu Arg Ser Asp Asp Thr Ala Val Tyr Tyr Cys
                85                  90                  95
Ala Arg Glu Ala Gln Leu Val Leu Tyr Tyr Tyr Tyr Gly Met Asp Val
            100                 105                 110

Trp Gly Gln Gly Thr Thr Val Thr Val Ser Ser
        115                 120

<210> SEQ ID NO 36
<211> LENGTH: 24
<212> TYPE: DNA
<213> ORGANISM: Artificial Sequence
<220> FEATURE:
<223> OTHER INFORMATION: Synthetic

<400> SEQUENCE: 36
ggttacactt ttacccatta tggt                                    24

<210> SEQ ID NO 37
<211> LENGTH: 8
<212> TYPE: PRT
<213> ORGANISM: Artificial Sequence
<220> FEATURE:
<223> OTHER INFORMATION: Synthetic

<400> SEQUENCE: 37

Gly Tyr Thr Phe Thr His Tyr Gly
1               5

<210> SEQ ID NO 38
<211> LENGTH: 24
<212> TYPE: DNA
<213> ORGANISM: Artificial Sequence
<220> FEATURE:
<223> OTHER INFORMATION: Synthetic

<400> SEQUENCE: 38
atcagcgctt acaatgatga caca                                    24

<210> SEQ ID NO 39
<211> LENGTH: 8
<212> TYPE: PRT
<213> ORGANISM: Artificial Sequence
<220> FEATURE:
<223> OTHER INFORMATION: Synthetic

<400> SEQUENCE: 39

Ile Ser Ala Tyr Asn Asp Asp Thr
1               5

<210> SEQ ID NO 40
<211> LENGTH: 48
<212> TYPE: DNA
<213> ORGANISM: Artificial Sequence
<220> FEATURE:
<223> OTHER INFORMATION: Synthetic

<400> SEQUENCE: 40
gcgagagaag cgcagctcgt cctctactac tactacggta tggacgtc          48

<210> SEQ ID NO 41
<211> LENGTH: 16
<212> TYPE: PRT
<213> ORGANISM: Artificial Sequence
<220> FEATURE:
<223> OTHER INFORMATION: Synthetic

<400> SEQUENCE: 41

Ala Arg Glu Ala Gln Leu Val Leu Tyr Tyr Tyr Tyr Gly Met Asp Val
1               5                   10                  15

<210> SEQ ID NO 42
<211> LENGTH: 322
<212> TYPE: DNA
<213> ORGANISM: Artificial Sequence
<220> FEATURE:
<223> OTHER INFORMATION: Synthetic

<400> SEQUENCE: 42

```
gaaattgtgt tgacacagtc tccagccacc ctgtctttgt ctccagggga aagagccacc      60
ctctcctgca gggccagtca gagtgttagc agcttcttag cctggaacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg cagtttatta ctgccagcag cgtaacaatt ggccgtacat ttttggccag     300
gggaccaagc tggagatcag ac                                              322
```

<210> SEQ ID NO 43
<211> LENGTH: 107
<212> TYPE: PRT
<213> ORGANISM: Artificial Sequence
<220> FEATURE:
<223> OTHER INFORMATION: Synthetic

<400> SEQUENCE: 43

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Phe
            20                  25                  30

Leu Ala Trp Asn Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Asn Asn Trp Pro Tyr
                85                  90                  95

Ile Phe Gly Gln Gly Thr Lys Leu Glu Ile Arg
            100                 105
```

<210> SEQ ID NO 44
<211> LENGTH: 18
<212> TYPE: DNA
<213> ORGANISM: Artificial Sequence
<220> FEATURE:
<223> OTHER INFORMATION: Synthetic

<400> SEQUENCE: 44

```
cagagtgtta gcagcttc                                                    18
```

<210> SEQ ID NO 45
<211> LENGTH: 6
<212> TYPE: PRT
<213> ORGANISM: Artificial Sequence
<220> FEATURE:
<223> OTHER INFORMATION: Synthetic

<400> SEQUENCE: 45

```
Gln Ser Val Ser Ser Phe
1               5
```

<210> SEQ ID NO 46

```
<211> LENGTH: 9
<212> TYPE: DNA
<213> ORGANISM: Artificial Sequence
<220> FEATURE:
<223> OTHER INFORMATION: Synthetic

<400> SEQUENCE: 46 gatgcatcc                                                                  9

<210> SEQ ID NO 47
<211> LENGTH: 3
<212> TYPE: PRT
<213> ORGANISM: Artificial Sequence
<220> FEATURE:
<223> OTHER INFORMATION: Synthetic

<400> SEQUENCE: 47

Asp Ala Ser
1

<210> SEQ ID NO 48
<211> LENGTH: 27
<212> TYPE: DNA
<213> ORGANISM: Artificial Sequence
<220> FEATURE:
<223> OTHER INFORMATION: Synthetic

<400> SEQUENCE: 48
cagcagcgta acaattggcc gtacatt                                             27

<210> SEQ ID NO 49
<211> LENGTH: 9
<212> TYPE: PRT
<213> ORGANISM: Artificial Sequence
<220> FEATURE:
<223> OTHER INFORMATION: Synthetic

<400> SEQUENCE: 49

Gln Gln Arg Asn Asn Trp Pro Tyr Ile
1               5

<210> SEQ ID NO 50
<211> LENGTH: 370
<212> TYPE: DNA
<213> ORGANISM: Artificial Sequence
<220> FEATURE:
<223> OTHER INFORMATION: Synthetic

<400> SEQUENCE: 50
caggttcagc tggtgcagtc tggagctgag gtgaagaagc ctggggcctc agtgaaggtc         60
tcctgcaagg cttctggtta cacctttacc agttatggta tcagctgggt gcgacaggcc        120
cctggacaag gcttgagtg atgggatgg atcagcgctt acaatgatga cacaaactat          180
gcacagaagt tccaggggag agtcaccatg accacagaca catccacgag cacagcctac        240
atggagctga ggagcctgag atctgacgac acggccgttt attactgtgc gagagaagcg        300
cagctcgtcc tctactacta ctacggtatg gacgtctggg gccaagggac cacggtcacc        360
gtctcctcag                                                              370

<210> SEQ ID NO 51
<211> LENGTH: 123
<212> TYPE: PRT
<213> ORGANISM: Artificial Sequence
<220> FEATURE:
<223> OTHER INFORMATION: Synthetic
```

<400> SEQUENCE: 51

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Asp Asp Thr Asn Tyr Ala Gln Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Ala Gln Leu Val Leu Tyr Tyr Tyr Gly Met Asp Val
            100                 105                 110

Trp Gly Gln Gly Thr Thr Val Thr Val Ser Ser
        115                 120

<210> SEQ ID NO 52
<211> LENGTH: 24
<212> TYPE: DNA
<213> ORGANISM: Artificial Sequence
<220> FEATURE:
<223> OTHER INFORMATION: Synthetic

<400> SEQUENCE: 52
ggttacacct ttaccagtta tggt                                    24

<210> SEQ ID NO 53
<211> LENGTH: 8
<212> TYPE: PRT
<213> ORGANISM: Artificial Sequence
<220> FEATURE:
<223> OTHER INFORMATION: Synthetic

<400> SEQUENCE: 53

Gly Tyr Thr Phe Thr Ser Tyr Gly
1               5

<210> SEQ ID NO 54
<211> LENGTH: 24
<212> TYPE: DNA
<213> ORGANISM: Artificial Sequence
<220> FEATURE:
<223> OTHER INFORMATION: Synthetic

<400> SEQUENCE: 54
atcagcgctt acaatgatga caca                                    24

<210> SEQ ID NO 55
<211> LENGTH: 8
<212> TYPE: PRT
<213> ORGANISM: Artificial Sequence
<220> FEATURE:
<223> OTHER INFORMATION: Synthetic

<400> SEQUENCE: 55

Ile Ser Ala Tyr Asn Asp Asp Thr
1               5

<210> SEQ ID NO 56

```
<211> LENGTH: 48
<212> TYPE: DNA
<213> ORGANISM: Artificial Sequence
<220> FEATURE:
<223> OTHER INFORMATION: Synthetic

<400> SEQUENCE: 56
gcgagagaag cgcagctcgt cctctactac tactacggta tggacgtc        48

<210> SEQ ID NO 57
<211> LENGTH: 16
<212> TYPE: PRT
<213> ORGANISM: Artificial Sequence
<220> FEATURE:
<223> OTHER INFORMATION: Synthetic

<400> SEQUENCE: 57

Ala Arg Glu Ala Gln Leu Val Leu Tyr Tyr Tyr Tyr Gly Met Asp Val
1               5                   10                  15

<210> SEQ ID NO 58
<211> LENGTH: 322
<212> TYPE: DNA
<213> ORGANISM: Artificial Sequence
<220> FEATURE:
<223> OTHER INFORMATION: Synthetic

<400> SEQUENCE: 58
gaaattgtgt tgacacagtc tccagccacc ctgtctttgt ctccagggga aagagccacc     60
ctctcctgca gggccagtca gagtgttagc agcttcttag cctggaacca acagaaacct    120
ggccaggctc ccaggctcct catctatgat gcatccaaca gggccactgg catcccagcc    180
aggttcagtg gcagtgggtc tgggacagac ttcactctca ccatcagcag cctagagcct    240
gaagattttg cagtttatta ctgccagcag cgtagcaatt ggccgtacat ttttggccag    300
gggaccaagc tggagatcaa ac                                             322

<210> SEQ ID NO 59
<211> LENGTH: 107
<212> TYPE: PRT
<213> ORGANISM: Artificial Sequence
<220> FEATURE:
<223> OTHER INFORMATION: Synthetic

<400> SEQUENCE: 59

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Phe
                20                  25                  30

Leu Ala Trp Asn Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Tyr
                85                  90                  95

Ile Phe Gly Gln Gly Thr Lys Leu Glu Ile Lys
            100                 105

<210> SEQ ID NO 60
<211> LENGTH: 18
```

<212> TYPE: DNA
<213> ORGANISM: Artificial Sequence
<220> FEATURE:
<223> OTHER INFORMATION: Synthetic

<400> SEQUENCE: 60
cagagtgtta gcagcttc                                                    18

<210> SEQ ID NO 61
<211> LENGTH: 6
<212> TYPE: PRT
<213> ORGANISM: Artificial Sequence
<220> FEATURE:
<223> OTHER INFORMATION: Synthetic

<400> SEQUENCE: 61

Gln Ser Val Ser Ser Phe
1               5

<210> SEQ ID NO 62
<211> LENGTH: 9
<212> TYPE: DNA
<213> ORGANISM: Artificial Sequence
<220> FEATURE:
<223> OTHER INFORMATION: Synthetic

<400> SEQUENCE: 62 gatgcatcc                                                               9

<210> SEQ ID NO 63
<211> LENGTH: 3
<212> TYPE: PRT
<213> ORGANISM: Artificial Sequence
<220> FEATURE:
<223> OTHER INFORMATION: Synthetic

<400> SEQUENCE: 63

Asp Ala Ser
1

<210> SEQ ID NO 64
<211> LENGTH: 27
<212> TYPE: DNA
<213> ORGANISM: Artificial Sequence
<220> FEATURE:
<223> OTHER INFORMATION: Synthetic

<400> SEQUENCE: 64
cagcagcgta gcaattggcc gtacatt                                           27

<210> SEQ ID NO 65
<211> LENGTH: 9
<212> TYPE: PRT
<213> ORGANISM: Artificial Sequence
<220> FEATURE:
<223> OTHER INFORMATION: Synthetic

<400> SEQUENCE: 65

Gln Gln Arg Ser Asn Trp Pro Tyr Ile
1               5

<210> SEQ ID NO 66
<211> LENGTH: 349
<212> TYPE: DNA
<213> ORGANISM: Artificial Sequence
<220> FEATURE:
<223> OTHER INFORMATION: Synthetic

<400> SEQUENCE: 66

```
gaagtgcagc tggtggagtc tgggggaggc ttggtacagc ctggcaggtc cctgagactc    60
tcctgtgcag cctctggatt cacctttgat gattatgccc tgcactgggt ccggcaagct   120
ccagggaagg gcctggagtg ggtctcaggt gttagtggaa tggtggtag aataggctat   180
gcggactctg tgaaaggccg attcaccatc tccagagaca acgccaagaa ctccctcttt   240
ctgcaaatga acagtctgag agttgaggac acggccttgt attattgtgc aaaaggccgg   300
gatgcttttg atatctgggg ccaagggaca ttggtcaccg tctcttcag              349
```

<210> SEQ ID NO 67
<211> LENGTH: 116
<212> TYPE: PRT
<213> ORGANISM: Artificial Sequence
<220> FEATURE:
<223> OTHER INFORMATION: Synthetic

<400> SEQUENCE: 67

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Leu His Trp Val Arg Gln Ala Pro Gly Lys Gly Leu Glu Trp Val
        35                  40                  45

Ser Gly Val Ser Trp Asn Gly Gly Arg Ile Gly Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Val Glu Asp Thr Ala Leu Tyr Tyr Cys
                85                  90                  95

Ala Lys Gly Arg Asp Ala Phe Asp Ile Trp Gly Gln Gly Thr Leu Val
            100                 105                 110

Thr Val Ser Ser
        115

<210> SEQ ID NO 68
<211> LENGTH: 24
<212> TYPE: DNA
<213> ORGANISM: Artificial Sequence
<220> FEATURE:
<223> OTHER INFORMATION: Synthetic

<400> SEQUENCE: 68

```
ggattcacct ttgatgatta tgcc                                            24
```

<210> SEQ ID NO 69
<211> LENGTH: 8
<212> TYPE: PRT
<213> ORGANISM: Artificial Sequence
<220> FEATURE:
<223> OTHER INFORMATION: Synthetic

<400> SEQUENCE: 69

Gly Phe Thr Phe Asp Asp Tyr Ala
1               5

<210> SEQ ID NO 70
<211> LENGTH: 24
<212> TYPE: DNA
<213> ORGANISM: Artificial Sequence
<220> FEATURE:
<223> OTHER INFORMATION: Synthetic

<400> SEQUENCE: 70
gttagttgga atggtggtag aata                                              24

<210> SEQ ID NO 71
<211> LENGTH: 8
<212> TYPE: PRT
<213> ORGANISM: Artificial Sequence
<220> FEATURE:
<223> OTHER INFORMATION: Synthetic

<400> SEQUENCE: 71

Val Ser Trp Asn Gly Gly Arg Ile
1               5

<210> SEQ ID NO 72
<211> LENGTH: 27
<212> TYPE: DNA
<213> ORGANISM: Artificial Sequence
<220> FEATURE:
<223> OTHER INFORMATION: Synthetic

<400> SEQUENCE: 72
gcaaaaggcc gggatgcttt tgatatc                                           27

<210> SEQ ID NO 73
<211> LENGTH: 9
<212> TYPE: PRT
<213> ORGANISM: Artificial Sequence
<220> FEATURE:
<223> OTHER INFORMATION: Synthetic

<400> SEQUENCE: 73

Ala Lys Gly Arg Asp Ala Phe Asp Ile
1               5

<210> SEQ ID NO 74
<211> LENGTH: 325
<212> TYPE: DNA
<213> ORGANISM: Artificial Sequence
<220> FEATURE:
<223> OTHER INFORMATION: Synthetic

<400> SEQUENCE: 74
gaaattgtgt tgacacagtc tccagccacc ctgtctttgt ctccagggga aagagccacc        60
ctctcctgca gggccagtca gagtgttagc agttacttag cctggtacca acagaaacct       120
ggccaggctc ccaggctcct catctatgat gcatccaaca gggccactgg catcccagcc       180
aggttcagtg gcagtgggtc tgggacagac ttcactctca ccatcagcag cctagagcct       240
gaagattttg catttttatta ctgtcagcag cgtaacaacc ggcctccatt cactttcggc       300
cctgggacca aagtggatgt cagac                                             325

<210> SEQ ID NO 75
<211> LENGTH: 108
<212> TYPE: PRT
<213> ORGANISM: Artificial Sequence
<220> FEATURE:
<223> OTHER INFORMATION: Synthetic

<400> SEQUENCE: 75

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Phe Tyr Tyr Cys Gln Gln Arg Asn Asn Arg Pro Pro
                85                  90                  95

Phe Thr Phe Gly Pro Gly Thr Lys Val Asp Val Arg
            100                 105

<210> SEQ ID NO 76
<211> LENGTH: 18
<212> TYPE: DNA
<213> ORGANISM: Artificial Sequence
<220> FEATURE:
<223> OTHER INFORMATION: Synthetic

<400> SEQUENCE: 76
cagagtgtta gcagttac                                                18

<210> SEQ ID NO 77
<211> LENGTH: 6
<212> TYPE: PRT
<213> ORGANISM: Artificial Sequence
<220> FEATURE:
<223> OTHER INFORMATION: Synthetic

<400> SEQUENCE: 77

Gln Ser Val Ser Ser Tyr
1               5

<210> SEQ ID NO 78
<211> LENGTH: 9
<212> TYPE: DNA
<213> ORGANISM: Artificial Sequence
<220> FEATURE:
<223> OTHER INFORMATION: Synthetic

<400> SEQUENCE: 78 gatgcatcc                                                           9

<210> SEQ ID NO 79
<211> LENGTH: 3
<212> TYPE: PRT
<213> ORGANISM: Artificial Sequence
<220> FEATURE:
<223> OTHER INFORMATION: Synthetic

<400> SEQUENCE: 79

Asp Ala Ser
1

<210> SEQ ID NO 80
<211> LENGTH: 30
<212> TYPE: DNA
<213> ORGANISM: Artificial Sequence
<220> FEATURE:
<223> OTHER INFORMATION: Synthetic

<400> SEQUENCE: 80
cagcagcgta caaccggcc tccattcact 30

<210> SEQ ID NO 81
<211> LENGTH: 10
<212> TYPE: PRT
<213> ORGANISM: Artificial Sequence
<220> FEATURE:
<223> OTHER INFORMATION: Synthetic

<400> SEQUENCE: 81

Gln Gln Arg Asn Asn Arg Pro Pro Phe Thr
1               5                   10

<210> SEQ ID NO 82
<211> LENGTH: 370
<212> TYPE: DNA
<213> ORGANISM: Artificial Sequence
<220> FEATURE:
<223> OTHER INFORMATION: Synthetic

<400> SEQUENCE: 82
caggttcagc tggtgcagtc tggagctgag gtgaagaagc ctggggcctc agtgaaggtc    60
tcctgtaagg cttctggttt caacttcttt cattatggta tcacctgggt gcgacaggcc   120
cctggacaag ggcttgagtg gatgggatgg atcagcactt acaatggtga cacaatctat   180
gcacagaagg tccagggcag agtcaccatg accacagaca cagccacgag cacggcctat   240
atggaactga ggagcctgag atctgacgac acggccgtgt attactgtgc gagatcggaa   300
cagcaggtgg actactactt ctacggtatg gacgtctggg gccaagggac cacggtcacc   360
gtttcctcag                                                         370

<210> SEQ ID NO 83
<211> LENGTH: 123
<212> TYPE: PRT
<213> ORGANISM: Artificial Sequence
<220> FEATURE:
<223> OTHER INFORMATION: Synthetic

<400> SEQUENCE: 83

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Phe Phe His Tyr
            20                  25                  30

Gly Ile Thr Trp Val Arg Gln Ala Pro Gly Gln Gly Leu Glu Trp Met
        35                  40                  45

Gly Trp Ile Ser Thr Tyr Asn Gly Asp Thr Ile Tyr Ala Gln Lys Val
    50                  55                  60

Gln Gly Arg Val Thr Met Thr Thr Asp Thr Ala Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ser Glu Gln Gln Val Asp Tyr Tyr Phe Tyr Gly Met Asp Val
            100                 105                 110

Trp Gly Gln Gly Thr Thr Val Thr Val Ser Ser
        115                 120

<210> SEQ ID NO 84
<211> LENGTH: 24
<212> TYPE: DNA
<213> ORGANISM: Artificial Sequence
<220> FEATURE:

<223> OTHER INFORMATION: Synthetic

<400> SEQUENCE: 84
ggtttcaact tctttcatta tggt                                              24

<210> SEQ ID NO 85
<211> LENGTH: 8
<212> TYPE: PRT
<213> ORGANISM: Artificial Sequence
<220> FEATURE:
<223> OTHER INFORMATION: Synthetic

<400> SEQUENCE: 85

Gly Phe Asn Phe Phe His Tyr Gly
1               5

<210> SEQ ID NO 86
<211> LENGTH: 24
<212> TYPE: DNA
<213> ORGANISM: Artificial Sequence
<220> FEATURE:
<223> OTHER INFORMATION: Synthetic

<400> SEQUENCE: 86
atcagcactt acaatggtga caca                                              24

<210> SEQ ID NO 87
<211> LENGTH: 8
<212> TYPE: PRT
<213> ORGANISM: Artificial Sequence
<220> FEATURE:
<223> OTHER INFORMATION: Synthetic

<400> SEQUENCE: 87

Ile Ser Thr Tyr Asn Gly Asp Thr
1               5

<210> SEQ ID NO 88
<211> LENGTH: 48
<212> TYPE: DNA
<213> ORGANISM: Artificial Sequence
<220> FEATURE:
<223> OTHER INFORMATION: Synthetic

<400> SEQUENCE: 88
gcgagatcgg aacagcaggt ggactactac ttctacggta tggacgtc                    48

<210> SEQ ID NO 89
<211> LENGTH: 16
<212> TYPE: PRT
<213> ORGANISM: Artificial Sequence
<220> FEATURE:
<223> OTHER INFORMATION: Synthetic

<400> SEQUENCE: 89

Ala Arg Ser Glu Gln Gln Val Asp Tyr Tyr Phe Tyr Gly Met Asp Val
1               5                   10                  15

<210> SEQ ID NO 90
<211> LENGTH: 325
<212> TYPE: DNA
<213> ORGANISM: Artificial Sequence
<220> FEATURE:
<223> OTHER INFORMATION: Synthetic

<400> SEQUENCE: 90

```
gaaattgtgt tgacacagtc tccagccacc ctgtctttgt ctccagggga aagagccacc      60
ctctcctgca gggccagtca gagtgttagc agttacttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg cattttatta ctgtcagcag cgtaacaacc ggcctccatt cactttcggc     300
cctgggacca agtggatgt cagac                                            325
```

```
<210> SEQ ID NO 91
<211> LENGTH: 108
<212> TYPE: PRT
<213> ORGANISM: Artificial Sequence
<220> FEATURE:
<223> OTHER INFORMATION: Synthetic

<400> SEQUENCE: 91

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Phe Tyr Tyr Cys Gln Gln Arg Asn Asn Arg Pro Pro
                85                  90                  95

Phe Thr Phe Gly Pro Gly Thr Lys Val Asp Val Arg
            100                 105
```

```
<210> SEQ ID NO 92
<211> LENGTH: 18
<212> TYPE: DNA
<213> ORGANISM: Artificial Sequence
<220> FEATURE:
<223> OTHER INFORMATION: Synthetic

<400> SEQUENCE: 92
cagagtgtta gcagttac                                                    18
```

```
<210> SEQ ID NO 93
<211> LENGTH: 6
<212> TYPE: PRT
<213> ORGANISM: Artificial Sequence
<220> FEATURE:
<223> OTHER INFORMATION: Synthetic

<400> SEQUENCE: 93

Gln Ser Val Ser Ser Tyr
1               5
```

```
<210> SEQ ID NO 94
<211> LENGTH: 9
<212> TYPE: DNA
<213> ORGANISM: Artificial Sequence
<220> FEATURE:
<223> OTHER INFORMATION: Synthetic

<400> SEQUENCE: 94 gatgcatcc                                                               9
```

<210> SEQ ID NO 95
<211> LENGTH: 3
<212> TYPE: PRT
<213> ORGANISM: Artificial Sequence
<220> FEATURE:
<223> OTHER INFORMATION: Synthetic

<400> SEQUENCE: 95

Asp Ala Ser
1

<210> SEQ ID NO 96
<211> LENGTH: 30
<212> TYPE: DNA
<213> ORGANISM: Artificial Sequence
<220> FEATURE:
<223> OTHER INFORMATION: Synthetic

<400> SEQUENCE: 96
cagcagcgta acaaccggcc tccattcact                                    30

<210> SEQ ID NO 97
<211> LENGTH: 10
<212> TYPE: PRT
<213> ORGANISM: Artificial Sequence
<220> FEATURE:
<223> OTHER INFORMATION: Synthetic

<400> SEQUENCE: 97

Gln Gln Arg Asn Asn Arg Pro Pro Phe Thr
1               5                   10

<210> SEQ ID NO 98
<211> LENGTH: 370
<212> TYPE: DNA
<213> ORGANISM: Artificial Sequence
<220> FEATURE:
<223> OTHER INFORMATION: Synthetic

<400> SEQUENCE: 98
caggttcagc tggtgcagtc tggagctgag gtgaagaagc ctggggcctc agtgaaggtc    60
tcctgtaagg cttctggttt caacttcttt cattatggta tcacctgggt gcgacaggcc   120
cctggacaag gcttgagtg gatgggatgg atcagcactt acaatggtga cacaatctat   180
gcacagaagg tccagggcag agtcaccatg accacagaca cagccacgag cacggcctat   240
atggaactga ggagcctgag atctgacgac acggccgtgt attactgtgc gagatcggaa   300
cagcaggtgg actactactt ctacggtatg gacgtctggg gccaagggac cacggtcacc   360
gtttcctcag                                                         370

<210> SEQ ID NO 99
<211> LENGTH: 123
<212> TYPE: PRT
<213> ORGANISM: Artificial Sequence
<220> FEATURE:
<223> OTHER INFORMATION: Synthetic

<400> SEQUENCE: 99

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Phe Phe His Tyr
            20                  25                  30

```
Gly Ile Thr Trp Val Arg Gln Ala Pro Gly Gln Gly Leu Glu Trp Met
            35                  40                  45

Gly Trp Ile Ser Thr Tyr Asn Gly Asp Thr Ile Tyr Ala Gln Lys Val
 50                  55                  60

Gln Gly Arg Val Thr Met Thr Thr Asp Thr Ala Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Ser Glu Gln Gln Val Asp Tyr Tyr Phe Tyr Gly Met Asp Val
            100                 105                 110

Trp Gly Gln Gly Thr Thr Val Thr Val Ser Ser
            115                 120

<210> SEQ ID NO 100
<211> LENGTH: 24
<212> TYPE: DNA
<213> ORGANISM: Artificial Sequence
<220> FEATURE:
<223> OTHER INFORMATION: Synthetic

<400> SEQUENCE: 100
ggtttcaact tctttcatta tggt                                          24

<210> SEQ ID NO 101
<211> LENGTH: 8
<212> TYPE: PRT
<213> ORGANISM: Artificial Sequence
<220> FEATURE:
<223> OTHER INFORMATION: Synthetic

<400> SEQUENCE: 101

Gly Phe Asn Phe Phe His Tyr Gly
 1               5

<210> SEQ ID NO 102
<211> LENGTH: 24
<212> TYPE: DNA
<213> ORGANISM: Artificial Sequence
<220> FEATURE:
<223> OTHER INFORMATION: Synthetic

<400> SEQUENCE: 102
atcagcactt acaatggtga caca                                          24

<210> SEQ ID NO 103
<211> LENGTH: 8
<212> TYPE: PRT
<213> ORGANISM: Artificial Sequence
<220> FEATURE:
<223> OTHER INFORMATION: Synthetic

<400> SEQUENCE: 103

Ile Ser Thr Tyr Asn Gly Asp Thr
 1               5

<210> SEQ ID NO 104
<211> LENGTH: 48
<212> TYPE: DNA
<213> ORGANISM: Artificial Sequence
<220> FEATURE:
<223> OTHER INFORMATION: Synthetic

<400> SEQUENCE: 104
gcgagatcgg aacagcaggt ggactactac ttctacggta tggacgtc                48
```

<210> SEQ ID NO 105
<211> LENGTH: 16
<212> TYPE: PRT
<213> ORGANISM: Artificial Sequence
<220> FEATURE:
<223> OTHER INFORMATION: Synthetic

<400> SEQUENCE: 105

Ala Arg Ser Glu Gln Gln Val Asp Tyr Tyr Phe Tyr Gly Met Asp Val
1               5                   10                  15

<210> SEQ ID NO 106
<211> LENGTH: 325
<212> TYPE: DNA
<213> ORGANISM: Artificial Sequence
<220> FEATURE:
<223> OTHER INFORMATION: Synthetic

<400> SEQUENCE: 106
gaaattgtgt tgacacagtc tccagccacc ctgtctttgt ctccagggga aagagccacc      60
ctctcctgca gggccagtca gagtgttagc agttacttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg catttattac tgtcagcag cgtaacaacc ggcctccatt cactttcggc      300
cctgggacca agtggatgt cagac                                            325

<210> SEQ ID NO 107
<211> LENGTH: 108
<212> TYPE: PRT
<213> ORGANISM: Artificial Sequence
<220> FEATURE:
<223> OTHER INFORMATION: Synthetic

<400> SEQUENCE: 107

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Phe Tyr Tyr Cys Gln Gln Arg Asn Asn Arg Pro Pro
                85                  90                  95

Phe Thr Phe Gly Pro Gly Thr Lys Val Asp Val Arg
            100                 105

<210> SEQ ID NO 108
<211> LENGTH: 18
<212> TYPE: DNA
<213> ORGANISM: Artificial Sequence
<220> FEATURE:
<223> OTHER INFORMATION: Synthetic

<400> SEQUENCE: 108
cagagtgtta gcagttac                                                    18

<210> SEQ ID NO 109
<211> LENGTH: 6
<212> TYPE: PRT
<213> ORGANISM: Artificial Sequence
<220> FEATURE:
<223> OTHER INFORMATION: Synthetic

<400> SEQUENCE: 109

Gln Ser Val Ser Ser Tyr
1               5

<210> SEQ ID NO 110
<211> LENGTH: 9
<212> TYPE: DNA
<213> ORGANISM: Artificial Sequence
<220> FEATURE:
<223> OTHER INFORMATION: Synthetic

<400> SEQUENCE: 110 gatgcatcc                                                                 9

<210> SEQ ID NO 111
<211> LENGTH: 3
<212> TYPE: PRT
<213> ORGANISM: Artificial Sequence
<220> FEATURE:
<223> OTHER INFORMATION: Synthetic

<400> SEQUENCE: 111

Asp Ala Ser
1

<210> SEQ ID NO 112
<211> LENGTH: 30
<212> TYPE: DNA
<213> ORGANISM: Artificial Sequence
<220> FEATURE:
<223> OTHER INFORMATION: Synthetic

<400> SEQUENCE: 112
cagcagcgta acaaccggcc tccattcact                                         30

<210> SEQ ID NO 113
<211> LENGTH: 10
<212> TYPE: PRT
<213> ORGANISM: Artificial Sequence
<220> FEATURE:
<223> OTHER INFORMATION: Synthetic

<400> SEQUENCE: 113

Gln Gln Arg Asn Asn Arg Pro Pro Phe Thr
1               5                   10

<210> SEQ ID NO 114
<211> LENGTH: 361
<212> TYPE: DNA
<213> ORGANISM: Artificial Sequence
<220> FEATURE:
<223> OTHER INFORMATION: Synthetic

<400> SEQUENCE: 114
caggtgcagc tggtgcagtc tggggctgag gtgaaagagc ctggggcctc agtgaagatc        60
tcctgcaagg cttctggata caccttcacc tcttatgata tcatctgggt gcgacaggcc      120
actggacaag ggcttgagtg gatgggatgg atgaacccaa acagtggtga cagaggctat      180

```
acacagaacc tccagggcag agtcaccttg accagggaca cctccataag tacagtctac    240
atggaactga gcagcctgag atctgaggac acggccgtat attattgtgc gcgagactac    300
agtaaccact actacggttt ggacgtctgg ggccaaggga ccacggtcac tgtctcctca    360
g                                                                    361
```

```
<210> SEQ ID NO 115
<211> LENGTH: 120
<212> TYPE: PRT
<213> ORGANISM: Artificial Sequence
<220> FEATURE:
<223> OTHER INFORMATION: Synthetic

<400> SEQUENCE: 115
```

Gln Val Gln Leu Val Gln Ser Gly Ala Glu Val Lys Glu Pro Gly Ala
1               5                   10                  15

Ser Val Lys Ile Ser Cys Lys Ala Ser Gly Tyr Thr Phe Thr Ser Tyr
            20                  25                  30

Asp Ile Ile Trp Val Arg Gln Ala Thr Gly Gln Gly Leu Glu Trp Met
        35                  40                  45

Gly Trp Met Asn Pro Asn Ser Gly Asp Arg Gly Tyr Thr Gln Asn Leu
    50                  55                  60

Gln Gly Arg Val Thr Leu Thr Arg Asp Thr Ser Ile Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Tyr Ser Asn His Tyr Tyr Gly Leu Asp Val Trp Gly Gln
            100                 105                 110

Gly Thr Thr Val Thr Val Ser Ser
        115                 120

```
<210> SEQ ID NO 116
<211> LENGTH: 24
<212> TYPE: DNA
<213> ORGANISM: Artificial Sequence
<220> FEATURE:
<223> OTHER INFORMATION: Synthetic

<400> SEQUENCE: 116
ggatacacct tcacctctta tgat                                            24

<210> SEQ ID NO 117
<211> LENGTH: 8
<212> TYPE: PRT
<213> ORGANISM: Artificial Sequence
<220> FEATURE:
<223> OTHER INFORMATION: Synthetic

<400> SEQUENCE: 117
```

Gly Tyr Thr Phe Thr Ser Tyr Asp
1               5

```
<210> SEQ ID NO 118
<211> LENGTH: 24
<212> TYPE: DNA
<213> ORGANISM: Artificial Sequence
<220> FEATURE:
<223> OTHER INFORMATION: Synthetic

<400> SEQUENCE: 118
atgaacccaa acagtggtga caga                                            24
```

<210> SEQ ID NO 119
<211> LENGTH: 8
<212> TYPE: PRT
<213> ORGANISM: Artificial Sequence
<220> FEATURE:
<223> OTHER INFORMATION: Synthetic

<400> SEQUENCE: 119

Met Asn Pro Asn Ser Gly Asp Arg
1               5

<210> SEQ ID NO 120
<211> LENGTH: 39
<212> TYPE: DNA
<213> ORGANISM: Artificial Sequence
<220> FEATURE:
<223> OTHER INFORMATION: Synthetic

<400> SEQUENCE: 120
gcgcgagact acagtaacca ctactacggt ttggacgtc                            39

<210> SEQ ID NO 121
<211> LENGTH: 13
<212> TYPE: PRT
<213> ORGANISM: Artificial Sequence
<220> FEATURE:
<223> OTHER INFORMATION: Synthetic

<400> SEQUENCE: 121

Ala Arg Asp Tyr Ser Asn His Tyr Tyr Gly Leu Asp Val
1               5                   10

<210> SEQ ID NO 122
<211> LENGTH: 322
<212> TYPE: DNA
<213> ORGANISM: Artificial Sequence
<220> FEATURE:
<223> OTHER INFORMATION: Synthetic

<400> SEQUENCE: 122
gacatccagt tgacccagtc tccatccttc ctgtctgcat ctgtaggaga cagagtcacc     60
atcacttgct gggccagtca ggacattagc aattatttag cctggtatca gcaaaaacca    120
gggaaagccc ctaagctcct gatctttgtt gcatccactt tgcagagtgg ggtcccatca    180
aggttcagcg gcagtggatc tgggacagaa ttcactctca caatcagtag cctgcagcct    240
gaagattttg caacttatta ctgtcaacag tttaatagtt acccgctcac tttcggcgga    300
gggaccaagg tggagatcag ac                                             322

<210> SEQ ID NO 123
<211> LENGTH: 107
<212> TYPE: PRT
<213> ORGANISM: Artificial Sequence
<220> FEATURE:
<223> OTHER INFORMATION: Synthetic

<400> SEQUENCE: 123

Asp Ile Gln Leu Thr Gln Ser Pro Ser Phe Leu Ser Ala Ser Val Gly
1               5                   10                  15

Asp Arg Val Thr Ile Thr Cys Trp Ala Ser Gln Asp Ile Ser Asn Tyr
            20                  25                  30

Leu Ala Trp Tyr Gln Gln Lys Pro Gly Lys Ala Pro Lys Leu Leu Ile
        35                  40                  45

```
Phe Val Ala Ser Thr Leu Gln Ser Gly Val Pro Ser Arg Phe Ser Gly
         50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Phe Asn Ser Tyr Pro Leu
                 85                  90                  95

Thr Phe Gly Gly Gly Thr Lys Val Glu Ile Arg
            100                 105
```

<210> SEQ ID NO 124
<211> LENGTH: 18
<212> TYPE: DNA
<213> ORGANISM: Artificial Sequence
<220> FEATURE:
<223> OTHER INFORMATION: Synthetic

<400> SEQUENCE: 124
caggacatta gcaattat                                             18

<210> SEQ ID NO 125
<211> LENGTH: 6
<212> TYPE: PRT
<213> ORGANISM: Artificial Sequence
<220> FEATURE:
<223> OTHER INFORMATION: Synthetic

<400> SEQUENCE: 125

```
Gln Asp Ile Ser Asn Tyr
 1               5
```

<210> SEQ ID NO 126
<211> LENGTH: 9
<212> TYPE: DNA
<213> ORGANISM: Artificial Sequence
<220> FEATURE:
<223> OTHER INFORMATION: Synthetic

<400> SEQUENCE: 126 gttgcatcc                                                        9

<210> SEQ ID NO 127
<211> LENGTH: 3
<212> TYPE: PRT
<213> ORGANISM: Artificial Sequence
<220> FEATURE:
<223> OTHER INFORMATION: Synthetic

<400> SEQUENCE: 127

```
Val Ala Ser
 1
```

<210> SEQ ID NO 128
<211> LENGTH: 30
<212> TYPE: DNA
<213> ORGANISM: Artificial Sequence
<220> FEATURE:
<223> OTHER INFORMATION: Synthetic

<400> SEQUENCE: 128
caacagttta atagttaccc gctcactttc                                30

<210> SEQ ID NO 129
<211> LENGTH: 9
<212> TYPE: PRT
<213> ORGANISM: Artificial Sequence
<220> FEATURE:
<223> OTHER INFORMATION: Synthetic

<400> SEQUENCE: 129

Gln Gln Phe Asn Ser Tyr Pro Leu Thr
1               5

<210> SEQ ID NO 130
<211> LENGTH: 370
<212> TYPE: DNA
<213> ORGANISM: Artificial Sequence
<220> FEATURE:
<223> OTHER INFORMATION: Synthetic

<400> SEQUENCE: 130
caggttcagc tggtgcagtc tggagctgag gtgaagaagc ctggggcctc agtgaaggtc      60
tcctgcaagg cttctggtta caccttacc agttatggta tcagctgggt gcgacaggcc     120
cctggacaag gcttgagtg gatgggatgg atcagcgctt acaatgatga cacaaactat     180
gcacagaagt tccaggggag agtcaccatg accacagaca catccacgag cacagcctac     240
atggagctga ggagcctgag atctgacgac acggccgttt attactgtgc gagagaagcg     300
cagctcgtcc tctactacta ctacggtatg gacgtctggg gccaagggac cacggtcacc     360
gtctcctcag                                                             370

<210> SEQ ID NO 131
<211> LENGTH: 123
<212> TYPE: PRT
<213> ORGANISM: Artificial Sequence
<220> FEATURE:
<223> OTHER INFORMATION: Synthetic

<400> SEQUENCE: 131

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Asp Asp Thr Asn Tyr Ala Gln Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Ala Gln Leu Val Leu Tyr Tyr Tyr Tyr Gly Met Asp Val
            100                 105                 110

Trp Gly Gln Gly Thr Thr Val Thr Val Ser Ser
        115                 120

<210> SEQ ID NO 132
<211> LENGTH: 24
<212> TYPE: DNA
<213> ORGANISM: Artificial Sequence
<220> FEATURE:
<223> OTHER INFORMATION: Synthetic

<400> SEQUENCE: 132
ggttacacct ttaccagtta tggt                                             24

```
<210> SEQ ID NO 133
<211> LENGTH: 8
<212> TYPE: PRT
<213> ORGANISM: Artificial Sequence
<220> FEATURE:
<223> OTHER INFORMATION: Synthetic

<400> SEQUENCE: 133

Gly Tyr Thr Phe Thr Ser Tyr Gly
1               5

<210> SEQ ID NO 134
<211> LENGTH: 24
<212> TYPE: DNA
<213> ORGANISM: Artificial Sequence
<220> FEATURE:
<223> OTHER INFORMATION: Synthetic

<400> SEQUENCE: 134
atcagcgctt acaatgatga caca                                           24

<210> SEQ ID NO 135
<211> LENGTH: 8
<212> TYPE: PRT
<213> ORGANISM: Artificial Sequence
<220> FEATURE:
<223> OTHER INFORMATION: Synthetic

<400> SEQUENCE: 135

Ile Ser Ala Tyr Asn Asp Asp Thr
1               5

<210> SEQ ID NO 136
<211> LENGTH: 48
<212> TYPE: DNA
<213> ORGANISM: Artificial Sequence
<220> FEATURE:
<223> OTHER INFORMATION: Synthetic

<400> SEQUENCE: 136
gcgagagaag cgcagctcgt cctctactac tactacggta tggacgtc                 48

<210> SEQ ID NO 137
<211> LENGTH: 16
<212> TYPE: PRT
<213> ORGANISM: Artificial Sequence
<220> FEATURE:
<223> OTHER INFORMATION: Synthetic

<400> SEQUENCE: 137

Ala Arg Glu Ala Gln Leu Val Leu Tyr Tyr Tyr Gly Met Asp Val
1               5                   10                  15

<210> SEQ ID NO 138
<211> LENGTH: 322
<212> TYPE: DNA
<213> ORGANISM: Artificial Sequence
<220> FEATURE:
<223> OTHER INFORMATION: Synthetic

<400> SEQUENCE: 138
gaaattgtgt tgacacagtc tccagccacc ctgtctttgt ctccagggga aagagccacc    60
ctctcctgca gggccagtca gagtgttagc agcttcttag cctggaacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
```
gaagattttg cagtttatta ctgccagcag cgtagcaatt ggccgtacat ttttggccag    300
gggaccaagc tggagatcaa ac                                             322

<210> SEQ ID NO 139
<211> LENGTH: 107
<212> TYPE: PRT
<213> ORGANISM: Artificial Sequence
<220> FEATURE:
<223> OTHER INFORMATION: Synthetic

<400> SEQUENCE: 139

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Phe
            20                  25                  30

Leu Ala Trp Asn Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Tyr
                85                  90                  95

Ile Phe Gly Gln Gly Thr Lys Leu Glu Ile Lys
            100                 105

<210> SEQ ID NO 140
<211> LENGTH: 18
<212> TYPE: DNA
<213> ORGANISM: Artificial Sequence
<220> FEATURE:
<223> OTHER INFORMATION: Synthetic

<400> SEQUENCE: 140
cagagtgtta gcagcttc                                                  18

<210> SEQ ID NO 141
<211> LENGTH: 6
<212> TYPE: PRT
<213> ORGANISM: Artificial Sequence
<220> FEATURE:
<223> OTHER INFORMATION: Synthetic

<400> SEQUENCE: 141

Gln Ser Val Ser Ser Phe
1               5

<210> SEQ ID NO 142
<211> LENGTH: 9
<212> TYPE: DNA
<213> ORGANISM: Artificial Sequence
<220> FEATURE:
<223> OTHER INFORMATION: Synthetic

<400> SEQUENCE: 142 gatgcatcc                                                             9

<210> SEQ ID NO 143
<211> LENGTH: 3
<212> TYPE: PRT
<213> ORGANISM: Artificial Sequence
<220> FEATURE:

<223> OTHER INFORMATION: Synthetic

<400> SEQUENCE: 143

Asp Ala Ser
1

<210> SEQ ID NO 144
<211> LENGTH: 27
<212> TYPE: DNA
<213> ORGANISM: Artificial Sequence
<220> FEATURE:
<223> OTHER INFORMATION: Synthetic

<400> SEQUENCE: 144
cagcagcgta gcaattggcc gtacatt                                              27

<210> SEQ ID NO 145
<211> LENGTH: 9
<212> TYPE: PRT
<213> ORGANISM: Artificial Sequence
<220> FEATURE:
<223> OTHER INFORMATION: Synthetic

<400> SEQUENCE: 145

Gln Gln Arg Ser Asn Trp Pro Tyr Ile
1               5

<210> SEQ ID NO 146
<211> LENGTH: 349
<212> TYPE: DNA
<213> ORGANISM: Artificial Sequence
<220> FEATURE:
<223> OTHER INFORMATION: Synthetic

<400> SEQUENCE: 146
gaagtgcagc tggtggagtc tgggggaggc ttggtacagc ctggcaggtc cctgagactc          60
tcctgtgcag cctctggatt cacctttgat gattatgccc tgcactgggt ccggcaagct         120
ccagggaagg gcctggagtg ggtctcaggt gttagttgga atggtggtag aataggctat         180
gcggactctg tgaaaggccg attcaccatc tccagagaca cgccaagaa ctccctcttt          240 ctgcaaatga acagtctgag agttgaggac acggccttgt attattgtgc aaaaggccgg         300
gatgcttttg atatctgggg ccaagggaca ttggtcaccg tctcttcag                    349

<210> SEQ ID NO 147
<211> LENGTH: 116
<212> TYPE: PRT
<213> ORGANISM: Artificial Sequence
<220> FEATURE:
<223> OTHER INFORMATION: Synthetic

<400> SEQUENCE: 147

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Leu His Trp Val Arg Gln Ala Pro Gly Lys Gly Leu Glu Trp Val
        35                  40                  45

Ser Gly Val Ser Trp Asn Gly Gly Arg Ile Gly Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Val Glu Asp Thr Ala Leu Tyr Tyr Cys
            85                  90                  95

Ala Lys Gly Arg Asp Ala Phe Asp Ile Trp Gly Gln Gly Thr Leu Val
        100                 105                 110

Thr Val Ser Ser
        115

<210> SEQ ID NO 148
<211> LENGTH: 24
<212> TYPE: DNA
<213> ORGANISM: Artificial Sequence
<220> FEATURE:
<223> OTHER INFORMATION: Synthetic

<400> SEQUENCE: 148
ggattcacct ttgatgatta tgcc                                          24

<210> SEQ ID NO 149
<211> LENGTH: 8
<212> TYPE: PRT
<213> ORGANISM: Artificial Sequence
<220> FEATURE:
<223> OTHER INFORMATION: Synthetic

<400> SEQUENCE: 149

Gly Phe Thr Phe Asp Asp Tyr Ala
1               5

<210> SEQ ID NO 150
<211> LENGTH: 24
<212> TYPE: DNA
<213> ORGANISM: Artificial Sequence
<220> FEATURE:
<223> OTHER INFORMATION: Synthetic

<400> SEQUENCE: 150
gttagttgga atggtggtag aata                                          24

<210> SEQ ID NO 151
<211> LENGTH: 8
<212> TYPE: PRT
<213> ORGANISM: Artificial Sequence
<220> FEATURE:
<223> OTHER INFORMATION: Synthetic

<400> SEQUENCE: 151

Val Ser Trp Asn Gly Gly Arg Ile
1               5

<210> SEQ ID NO 152
<211> LENGTH: 27
<212> TYPE: DNA
<213> ORGANISM: Artificial Sequence
<220> FEATURE:
<223> OTHER INFORMATION: Synthetic

<400> SEQUENCE: 152
gcaaaaggcc gggatgcttt tgatatc                                       27

<210> SEQ ID NO 153
<211> LENGTH: 9
<212> TYPE: PRT
<213> ORGANISM: Artificial Sequence
<220> FEATURE:
<223> OTHER INFORMATION: Synthetic

<400> SEQUENCE: 153

Ala Lys Gly Arg Asp Ala Phe Asp Ile
1               5

<210> SEQ ID NO 154
<211> LENGTH: 322
<212> TYPE: DNA
<213> ORGANISM: Artificial Sequence
<220> FEATURE:
<223> OTHER INFORMATION: Synthetic

<400> SEQUENCE: 154

```
gacatccaga tgacccagtc tccatcttcc gtgtctgcat ctgtaggaga cagagtcacc      60
atcacttgtc gggcgagtca gggtattagc agctggttag cctggtatca gcagaaacca     120
gggaaagccc ctaaactcct gatctatgct gcatccagtt tgcaaagtgg ggtcccatca     180
aggttcagcg gcagtggatc tgggacagat ttcactctca ccatcagcag cctgcagcct     240
gaagattttg caacttacta ttgtcaacat gcttacagtt tcccgtacac ttttggccag     300
gggaccaagc tggagatcaa ac                                              322
```

<210> SEQ ID NO 155
<211> LENGTH: 107
<212> TYPE: PRT
<213> ORGANISM: Artificial Sequence
<220> FEATURE:
<223> OTHER INFORMATION: Synthetic

<400> SEQUENCE: 155

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Ala Tyr Ser Phe Pro Tyr
                85                  90                  95

Thr Phe Gly Gln Gly Thr Lys Leu Glu Ile Lys
            100                 105

<210> SEQ ID NO 156
<211> LENGTH: 18
<212> TYPE: DNA
<213> ORGANISM: Artificial Sequence
<220> FEATURE:
<223> OTHER INFORMATION: Synthetic

<400> SEQUENCE: 156

```
cagggtatta gcagctgg                                                    18
```

<210> SEQ ID NO 157
<211> LENGTH: 6
<212> TYPE: PRT
<213> ORGANISM: Artificial Sequence
<220> FEATURE:
<223> OTHER INFORMATION: Synthetic

<400> SEQUENCE: 157

```
Gln Gly Ile Ser Ser Trp
1               5
```

<210> SEQ ID NO 158
<211> LENGTH: 9
<212> TYPE: DNA
<213> ORGANISM: Artificial Sequence
<220> FEATURE:
<223> OTHER INFORMATION: Synthetic

<400> SEQUENCE: 158 gctgcatcc                                                                9

<210> SEQ ID NO 159
<211> LENGTH: 3
<212> TYPE: PRT
<213> ORGANISM: Artificial Sequence
<220> FEATURE:
<223> OTHER INFORMATION: Synthetic

<400> SEQUENCE: 159

```
Ala Ala Ser
1
```

<210> SEQ ID NO 160
<211> LENGTH: 27
<212> TYPE: DNA
<213> ORGANISM: Artificial Sequence
<220> FEATURE:
<223> OTHER INFORMATION: Synthetic

<400> SEQUENCE: 160
caacatgctt acagtttccc gtacact                                           27

<210> SEQ ID NO 161
<211> LENGTH: 9
<212> TYPE: PRT
<213> ORGANISM: Artificial Sequence
<220> FEATURE:
<223> OTHER INFORMATION: Synthetic

<400> SEQUENCE: 161

```
Gln His Ala Tyr Ser Phe Pro Tyr Thr
1               5
```

<210> SEQ ID NO 162
<211> LENGTH: 349
<212> TYPE: DNA
<213> ORGANISM: Artificial Sequence
<220> FEATURE:
<223> OTHER INFORMATION: Synthetic

<400> SEQUENCE: 162
gaagtgcagc tggtggagtc tgggggaggc ttggtacagc ctggcaggtc cctgagactc        60
tcctgtgcag cctctggatt cacctttgat gattatgcct tgcactgggt ccggcaagct      120
ccagggaagg gcctggagtg ggtctcaggt attagttgga acagtggtag aataggctat      180
gcggactctg tgaagggccg attcaccatt tccagagaca cgccaagaa ctccctcttt       240
ctgcaaatga acagtctgag agctgaggac acggccttgt attattgtgc aaaaggccgg      300
gatgcttttg atatctgggg ccaagggaca ttggtcaccg tctcttcag                  349

<210> SEQ ID NO 163
<211> LENGTH: 116

<212> TYPE: PRT
<213> ORGANISM: Artificial Sequence
<220> FEATURE:
<223> OTHER INFORMATION: Synthetic

<400> SEQUENCE: 163

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Leu His Trp Val Arg Gln Ala Pro Gly Lys Gly Leu Glu Trp Val
        35                  40                  45

Ser Gly Ile Ser Trp Asn Ser Gly Arg Ile Gly Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Leu Tyr Tyr Cys
                85                  90                  95

Ala Lys Gly Arg Asp Ala Phe Asp Ile Trp Gly Gln Gly Thr Leu Val
            100                 105                 110

Thr Val Ser Ser
        115

<210> SEQ ID NO 164
<211> LENGTH: 24
<212> TYPE: DNA
<213> ORGANISM: Artificial Sequence
<220> FEATURE:
<223> OTHER INFORMATION: Synthetic

<400> SEQUENCE: 164
ggattcacct ttgatgatta tgcc                                          24

<210> SEQ ID NO 165
<211> LENGTH: 8
<212> TYPE: PRT
<213> ORGANISM: Artificial Sequence
<220> FEATURE:
<223> OTHER INFORMATION: Synthetic

<400> SEQUENCE: 165

Gly Phe Thr Phe Asp Asp Tyr Ala
1               5

<210> SEQ ID NO 166
<211> LENGTH: 24
<212> TYPE: DNA
<213> ORGANISM: Artificial Sequence
<220> FEATURE:
<223> OTHER INFORMATION: Synthetic

<400> SEQUENCE: 166
attagttgga acagtggtag aata                                          24

<210> SEQ ID NO 167
<211> LENGTH: 8
<212> TYPE: PRT
<213> ORGANISM: Artificial Sequence
<220> FEATURE:
<223> OTHER INFORMATION: Synthetic

<400> SEQUENCE: 167

Ile Ser Trp Asn Ser Gly Arg Ile

<210> SEQ ID NO 168
<211> LENGTH: 27
<212> TYPE: DNA
<213> ORGANISM: Artificial Sequence
<220> FEATURE:
<223> OTHER INFORMATION: Synthetic

<400> SEQUENCE: 168
gcaaaaggcc gggatgcttt tgatatc                                          27

<210> SEQ ID NO 169
<211> LENGTH: 9
<212> TYPE: PRT
<213> ORGANISM: Artificial Sequence
<220> FEATURE:
<223> OTHER INFORMATION: Synthetic

<400> SEQUENCE: 169

Ala Lys Gly Arg Asp Ala Phe Asp Ile
1               5

<210> SEQ ID NO 170
<211> LENGTH: 322
<212> TYPE: DNA
<213> ORGANISM: Artificial Sequence
<220> FEATURE:
<223> OTHER INFORMATION: Synthetic

<400> SEQUENCE: 170
gacatccaga tgacccagtc tccatcttcc gtgtctgcat ctgtaggaga cagagtcacc      60
atcacttgtc gggcgagtca gggtattagc agctggttag cctggtatca gcagaaacca     120
gggaaagccc ctaagctcct gatctatgct gcatccagtt tgcaaagtgg ggtcccatca     180
aggttcagcg gcagtggatc tgggacagat tcactctca ccatcagcag cctgcagcct     240
gaagattttg caacttacta ttgtcaacag gctaacagtt tcccgtacac ttttggccag     300
gggaccaagc tggagatcaa ac                                             322

<210> SEQ ID NO 171
<211> LENGTH: 107
<212> TYPE: PRT
<213> ORGANISM: Artificial Sequence
<220> FEATURE:
<223> OTHER INFORMATION: Synthetic

<400> SEQUENCE: 171

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Tyr
                85                  90                  95

Thr Phe Gly Gln Gly Thr Lys Leu Glu Ile Lys
            100                 105

<210> SEQ ID NO 172
<211> LENGTH: 18
<212> TYPE: DNA
<213> ORGANISM: Artificial Sequence
<220> FEATURE:
<223> OTHER INFORMATION: Synthetic

<400> SEQUENCE: 172
cagggtatta gcagctgg                                                   18

<210> SEQ ID NO 173
<211> LENGTH: 6
<212> TYPE: PRT
<213> ORGANISM: Artificial Sequence
<220> FEATURE:
<223> OTHER INFORMATION: Synthetic

<400> SEQUENCE: 173

Gln Gly Ile Ser Ser Trp
1               5

<210> SEQ ID NO 174
<211> LENGTH: 9
<212> TYPE: DNA
<213> ORGANISM: Artificial Sequence
<220> FEATURE:
<223> OTHER INFORMATION: Synthetic

<400> SEQUENCE: 174 gctgcatcc                                                              9

<210> SEQ ID NO 175
<211> LENGTH: 3
<212> TYPE: PRT
<213> ORGANISM: Artificial Sequence
<220> FEATURE:
<223> OTHER INFORMATION: Synthetic

<400> SEQUENCE: 175

Ala Ala Ser
1

<210> SEQ ID NO 176
<211> LENGTH: 27
<212> TYPE: DNA
<213> ORGANISM: Artificial Sequence
<220> FEATURE:
<223> OTHER INFORMATION: Synthetic

<400> SEQUENCE: 176
caacaggcta acagtttccc gtacact                                         27

<210> SEQ ID NO 177
<211> LENGTH: 9
<212> TYPE: PRT
<213> ORGANISM: Artificial Sequence
<220> FEATURE:
<223> OTHER INFORMATION: Synthetic

<400> SEQUENCE: 177

Gln Gln Ala Asn Ser Phe Pro Tyr Thr
1               5

<210> SEQ ID NO 178
<211> LENGTH: 361

<212> TYPE: DNA
<213> ORGANISM: Artificial Sequence
<220> FEATURE:
<223> OTHER INFORMATION: Synthetic

<400> SEQUENCE: 178

```
caggtgcagc tggtgcagtc tggggctgag gtgaaagagc ctggggcctc agtgaaggtc    60
tcctgcaagg cttctggata caccttcacc tcttatgata tcatctgggt gcgacaggcc   120
actggacaag gcttgagtg gatgggatgg atgaacccaa acagtggtaa cacaggctat   180
acacagaacc tccagggcag agtcaccttg accaggaaca cctccataac tacagtctac   240
atggaactga gcagcctgag ctctgaggac acggccgttt attactgtgc gcagactac   300
agtagccact actacggttt ggacgtctgg ggccaaggga ccacggtcac cgtctcctca   360
a                                                                   361
```

<210> SEQ ID NO 179
<211> LENGTH: 120
<212> TYPE: PRT
<213> ORGANISM: Artificial Sequence
<220> FEATURE:
<223> OTHER INFORMATION: Synthetic

<400> SEQUENCE: 179

```
Gln Val Gln Leu Val Gln Ser Gly Ala Glu Val Lys Glu Pro Gly Ala
1               5                  10                  15

Ser Val Lys Val Ser Cys Lys Ala Ser Gly Tyr Thr Phe Thr Ser Tyr
            20                  25                  30

Asp Ile Ile Trp Val Arg Gln Ala Thr Gly Gln Gly Leu Glu Trp Met
        35                  40                  45

Gly Trp Met Asn Pro Asn Ser Gly Asn Thr Gly Tyr Thr Gln Asn Leu
    50                  55                  60

Gln Gly Arg Val Thr Leu Thr Arg Asn Thr Ser Ile Thr Thr Val Tyr
65                  70                  75                  80

Met Glu Leu Ser Ser Leu Ser Ser Glu Asp Thr Ala Val Tyr Tyr Cys
                85                  90                  95

Ala Arg Asp Tyr Ser Ser His Tyr Tyr Gly Leu Asp Val Trp Gly Gln
            100                 105                 110

Gly Thr Thr Val Thr Val Ser Ser
        115                 120
```

<210> SEQ ID NO 180
<211> LENGTH: 24
<212> TYPE: DNA
<213> ORGANISM: Artificial Sequence
<220> FEATURE:
<223> OTHER INFORMATION: Synthetic

<400> SEQUENCE: 180

```
ggatacacct tcacctctta tgat                                           24
```

<210> SEQ ID NO 181
<211> LENGTH: 8
<212> TYPE: PRT
<213> ORGANISM: Artificial Sequence
<220> FEATURE:
<223> OTHER INFORMATION: Synthetic

<400> SEQUENCE: 181

```
Gly Tyr Thr Phe Thr Ser Tyr Asp
1               5
```

<210> SEQ ID NO 182
<211> LENGTH: 24
<212> TYPE: DNA
<213> ORGANISM: Artificial Sequence
<220> FEATURE:
<223> OTHER INFORMATION: Synthetic

<400> SEQUENCE: 182
atgaacccaa acagtggtaa caca                                          24

<210> SEQ ID NO 183
<211> LENGTH: 8
<212> TYPE: PRT
<213> ORGANISM: Artificial Sequence
<220> FEATURE:
<223> OTHER INFORMATION: Synthetic

<400> SEQUENCE: 183

Met Asn Pro Asn Ser Gly Asn Thr
1               5

<210> SEQ ID NO 184
<211> LENGTH: 39
<212> TYPE: DNA
<213> ORGANISM: Artificial Sequence
<220> FEATURE:
<223> OTHER INFORMATION: Synthetic

<400> SEQUENCE: 184
gcgcgagact acagtagcca ctactacggt ttggacgtc                          39

<210> SEQ ID NO 185
<211> LENGTH: 13
<212> TYPE: PRT
<213> ORGANISM: Artificial Sequence
<220> FEATURE:
<223> OTHER INFORMATION: Synthetic

<400> SEQUENCE: 185

Ala Arg Asp Tyr Ser Ser His Tyr Tyr Gly Leu Asp Val
1               5                   10

<210> SEQ ID NO 186
<211> LENGTH: 322
<212> TYPE: DNA
<213> ORGANISM: Artificial Sequence
<220> FEATURE:
<223> OTHER INFORMATION: Synthetic

<400> SEQUENCE: 186
gacatccagt tgacccagtc tccatccttc ctgtctacat ctataggaga cagagtcacc    60
atcacttgct gggccagtca ggacattagc aattatttag cctggtatca gcaaaaacca   120
gggaaagccc ctaagctcct gatctttgtt gcatccactt tgcagagtgg ggtcccatca   180
aggttcagcg gcagtggatc tgggacagaa ttcactctca caatcagtag cctgcagcct   240
gaggattttg caacttatta ctgtcaacag tttaatagtt acccgctcac tttcggcgga   300
gggaccaagg tggaaatcaa ac                                           322

<210> SEQ ID NO 187
<211> LENGTH: 107
<212> TYPE: PRT
<213> ORGANISM: Artificial Sequence
<220> FEATURE:

<223> OTHER INFORMATION: Synthetic

<400> SEQUENCE: 187

Asp Ile Gln Leu Thr Gln Ser Pro Ser Phe Leu Ser Thr Ser Ile Gly
1               5                   10                  15

Asp Arg Val Thr Ile Thr Cys Trp Ala Ser Gln Asp Ile Ser Asn Tyr
            20                  25                  30

Leu Ala Trp Tyr Gln Gln Lys Pro Gly Lys Ala Pro Lys Leu Leu Ile
        35                  40                  45

Phe Val Ala Ser Thr Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105

<210> SEQ ID NO 188
<211> LENGTH: 18
<212> TYPE: DNA
<213> ORGANISM: Artificial Sequence
<220> FEATURE:
<223> OTHER INFORMATION: Synthetic

<400> SEQUENCE: 188
caggacatta gcaattat                                                 18

<210> SEQ ID NO 189
<211> LENGTH: 6
<212> TYPE: PRT
<213> ORGANISM: Artificial Sequence
<220> FEATURE:
<223> OTHER INFORMATION: Synthetic

<400> SEQUENCE: 189

Gln Asp Ile Ser Asn Tyr
1               5

<210> SEQ ID NO 190
<211> LENGTH: 9
<212> TYPE: DNA
<213> ORGANISM: Artificial Sequence
<220> FEATURE:
<223> OTHER INFORMATION: Synthetic

<400> SEQUENCE: 190 gttgcatcc                                                            9

<210> SEQ ID NO 191
<211> LENGTH: 3
<212> TYPE: PRT
<213> ORGANISM: Artificial Sequence
<220> FEATURE:
<223> OTHER INFORMATION: Synthetic

<400> SEQUENCE: 191

Val Ala Ser
1

<210> SEQ ID NO 192
<211> LENGTH: 30
<212> TYPE: DNA

<213> ORGANISM: Artificial Sequence
<220> FEATURE:
<223> OTHER INFORMATION: Synthetic

<400> SEQUENCE: 192

```
caacagttta atagttaccc gctcactttc                                        30
```

<210> SEQ ID NO 193
<211> LENGTH: 10
<212> TYPE: PRT
<213> ORGANISM: Artificial Sequence
<220> FEATURE:
<223> OTHER INFORMATION: Synthetic

<400> SEQUENCE: 193

Gln Gln Phe Asn Ser Tyr Pro Leu Thr Phe
1               5                   10

<210> SEQ ID NO 194
<211> LENGTH: 378
<212> TYPE: DNA
<213> ORGANISM: Artificial Sequence
<220> FEATURE:
<223> OTHER INFORMATION: Synthetic

<400> SEQUENCE: 194

```
caggtccagc tggtgcagtc tgggggagac ttggtacagc ccggcaggtc cctgagactc       60
tcctgtgcag cctctggatt cacctttgat gattatgcca tgcactgggt ccggcaaact      120
ccagggaagg gcctggagtg gtctcaggt attagttgga atagtggggc cataggctat       180
gcggactctg tgaagggccg attcaccatc tccagagaca cgccaagaa ctccctgtat       240
ctgcaaatga acagtctgag agctgaggac acggccttgt attactgtac aaaagaagaa      300
gtgggagcta cggtggatta tttctacttc tacggtatgg acgtctgggg ccaagggacc      360
acggtcaccg tctcctca                                                   378
```

<210> SEQ ID NO 195
<211> LENGTH: 126
<212> TYPE: PRT
<213> ORGANISM: Artificial Sequence
<220> FEATURE:
<223> OTHER INFORMATION: Synthetic

<400> SEQUENCE: 195

Gln Val Gln Leu Val Gln Ser Gly Gly Asp Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Thr Pro Gly Lys Gly Leu Glu Trp Val
        35                  40                  45

Ser Gly Ile Ser Trp Asn Ser Gly Ala Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Thr Lys Glu Glu Val Gly Ala Thr Val Asp Tyr Phe Tyr Phe Tyr Gly
            100                 105                 110

Met Asp Val Trp Gly Gln Gly Thr Thr Val Thr Val Ser Ser
        115                 120                 125

<210> SEQ ID NO 196
<211> LENGTH: 24
<212> TYPE: DNA
<213> ORGANISM: Artificial Sequence
<220> FEATURE:
<223> OTHER INFORMATION: Synthetic

<400> SEQUENCE: 196
ggattcacct ttgatgatta tgcc                                    24

<210> SEQ ID NO 197
<211> LENGTH: 8
<212> TYPE: PRT
<213> ORGANISM: Artificial Sequence
<220> FEATURE:
<223> OTHER INFORMATION: Synthetic

<400> SEQUENCE: 197

Gly Phe Thr Phe Asp Asp Tyr Ala
1               5

<210> SEQ ID NO 198
<211> LENGTH: 24
<212> TYPE: DNA
<213> ORGANISM: Artificial Sequence
<220> FEATURE:
<223> OTHER INFORMATION: Synthetic

<400> SEQUENCE: 198
attagttgga atagtggggc cata                                    24

<210> SEQ ID NO 199
<211> LENGTH: 8
<212> TYPE: PRT
<213> ORGANISM: Artificial Sequence
<220> FEATURE:
<223> OTHER INFORMATION: Synthetic

<400> SEQUENCE: 199

Ile Ser Trp Asn Ser Gly Ala Ile
1               5

<210> SEQ ID NO 200
<211> LENGTH: 57
<212> TYPE: DNA
<213> ORGANISM: Artificial Sequence
<220> FEATURE:
<223> OTHER INFORMATION: Synthetic

<400> SEQUENCE: 200
acaaaagaag aagtgggagc tacggtggat tatttctact tctacggtat ggacgtc    57

<210> SEQ ID NO 201
<211> LENGTH: 19
<212> TYPE: PRT
<213> ORGANISM: Artificial Sequence
<220> FEATURE:
<223> OTHER INFORMATION: Synthetic

<400> SEQUENCE: 201

Thr Lys Glu Glu Val Gly Ala Thr Val Asp Tyr Phe Tyr Phe Tyr Gly
1               5                   10                  15

Met Asp Val

<210> SEQ ID NO 202

<211> LENGTH: 318
<212> TYPE: DNA
<213> ORGANISM: Artificial Sequence
<220> FEATURE:
<223> OTHER INFORMATION: Synthetic

<400> SEQUENCE: 202

```
gaaattgtga tgactcagtc tccagccacc ctgtctttgt ctccagggga aagagccacc    60
ctctcctgct gggccagtca gagtgttagc aactacttag cctggtacca acagaaacct   120
ggccaggctc ccagactcct catctatgat gcatccaaca gggccactgg catcccagcc   180
aggttcagtg gcagtgggtc tgggacagac ttcactctca ccatcagcag cctagagcct   240
gaagattttg cagtttatta ctgtcagcag cgtagcaact ggcctacgtt cggccaaggg   300
accaaggtgg aaatcaaa                                                 318
```

<210> SEQ ID NO 203
<211> LENGTH: 106
<212> TYPE: PRT
<213> ORGANISM: Artificial Sequence
<220> FEATURE:
<223> OTHER INFORMATION: Synthetic

<400> SEQUENCE: 203

```
Glu Ile Val Met Thr Gln Ser Pro Ala Thr Leu Ser Leu Ser Pro Gly
1               5                   10                  15
Glu Arg Ala Thr Leu Ser Cys Trp Ala Ser Gln Ser Val Ser Asn Tyr
            20                  25                  30
Leu Ala Trp Tyr Gln Gln Lys Pro Gly Gln Ala Pro Arg Leu Leu Ile
        35                  40                  45
Tyr Asp Ala Ser Asn Arg Ala Thr Gly Ile Pro Ala Arg Phe Ser Gly
    50                  55                  60
Ser Gly Ser Gly Thr Asp Phe Thr Leu Thr Ile Ser Ser Leu Glu Pro
65                  70                  75                  80
Glu Asp Phe Ala Val Tyr Tyr Cys Gln Gln Arg Ser Asn Trp Pro Thr
                85                  90                  95
Phe Gly Gln Gly Thr Lys Val Glu Ile Lys
            100                 105
```

<210> SEQ ID NO 204
<211> LENGTH: 18
<212> TYPE: DNA
<213> ORGANISM: Artificial Sequence
<220> FEATURE:
<223> OTHER INFORMATION: Synthetic

<400> SEQUENCE: 204

```
cagagtgtta gcaactac                                                  18
```

<210> SEQ ID NO 205
<211> LENGTH: 6
<212> TYPE: PRT
<213> ORGANISM: Artificial Sequence
<220> FEATURE:
<223> OTHER INFORMATION: Synthetic

<400> SEQUENCE: 205

```
Gln Ser Val Ser Asn Tyr
1               5
```

<210> SEQ ID NO 206
<211> LENGTH: 9

<212> TYPE: DNA
<213> ORGANISM: Artificial Sequence
<220> FEATURE:
<223> OTHER INFORMATION: Synthetic

<400> SEQUENCE: 206 gatgcatcc                                                              9

<210> SEQ ID NO 207
<211> LENGTH: 3
<212> TYPE: PRT
<213> ORGANISM: Artificial Sequence
<220> FEATURE:
<223> OTHER INFORMATION: Synthetic

<400> SEQUENCE: 207

Asp Ala Ser
1

<210> SEQ ID NO 208
<211> LENGTH: 24
<212> TYPE: DNA
<213> ORGANISM: Artificial Sequence
<220> FEATURE:
<223> OTHER INFORMATION: Synthetic

<400> SEQUENCE: 208
cagcagcgta gcaactggcc tacg                                            24

<210> SEQ ID NO 209
<211> LENGTH: 8
<212> TYPE: PRT
<213> ORGANISM: Artificial Sequence
<220> FEATURE:
<223> OTHER INFORMATION: Synthetic

<400> SEQUENCE: 209

Gln Gln Arg Ser Asn Trp Pro Thr
1               5

<210> SEQ ID NO 210
<211> LENGTH: 348
<212> TYPE: DNA
<213> ORGANISM: Artificial Sequence
<220> FEATURE:
<223> OTHER INFORMATION: Synthetic

<400> SEQUENCE: 210
caagtgcagc tggtgcagtc tgggggaggc ttggtacagc ctggcaggtc cctgagactc      60
tcctgtgcag cctctggatt cacctttgat gattatgcca tgcactgggt ccggcaagct     120
ccagggaagg gcctggagtg ggtctcaggt attagttgga atagtggtag ggtaggctat     180
gcggactctg tgaagggccg attcaccatc tccagagaca acgccaagaa ctccctgtat     240
ctgcaaatga acagtctgag agctgaggac acggccttgt attactgtac aaaaggccgg     300
gatgcttttg atatctgggg ccaggggaca atggtcaccg tctcttca                 348

<210> SEQ ID NO 211
<211> LENGTH: 116
<212> TYPE: PRT
<213> ORGANISM: Artificial Sequence
<220> FEATURE:
<223> OTHER INFORMATION: Synthetic

<400> SEQUENCE: 211

-continued

Gln Val Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Arg Val Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Thr Lys Gly Arg Asp Ala Phe Asp Ile Trp Gly Gln Gly Thr Met Val
            100                 105                 110

Thr Val Ser Ser
        115

<210> SEQ ID NO 212
<211> LENGTH: 24
<212> TYPE: DNA
<213> ORGANISM: Artificial Sequence
<220> FEATURE:
<223> OTHER INFORMATION: Synthetic

<400> SEQUENCE: 212
ggattcacct ttgatgatta tgcc                                              24

<210> SEQ ID NO 213
<211> LENGTH: 8
<212> TYPE: PRT
<213> ORGANISM: Artificial Sequence
<220> FEATURE:
<223> OTHER INFORMATION: Synthetic

<400> SEQUENCE: 213

Gly Phe Thr Phe Asp Asp Tyr Ala
1               5

<210> SEQ ID NO 214
<211> LENGTH: 24
<212> TYPE: DNA
<213> ORGANISM: Artificial Sequence
<220> FEATURE:
<223> OTHER INFORMATION: Synthetic

<400> SEQUENCE: 214
attagttgga atagtggtag ggta                                              24

<210> SEQ ID NO 215
<211> LENGTH: 8
<212> TYPE: PRT
<213> ORGANISM: Artificial Sequence
<220> FEATURE:
<223> OTHER INFORMATION: Synthetic

<400> SEQUENCE: 215

Ile Ser Trp Asn Ser Gly Arg Val
1               5

<210> SEQ ID NO 216
<211> LENGTH: 27
<212> TYPE: DNA
<213> ORGANISM: Artificial Sequence
<220> FEATURE:
<223> OTHER INFORMATION: Synthetic

<400> SEQUENCE: 216
acaaaaggcc gggatgcttt tgatatc                                        27

<210> SEQ ID NO 217
<211> LENGTH: 9
<212> TYPE: PRT
<213> ORGANISM: Artificial Sequence
<220> FEATURE:
<223> OTHER INFORMATION: Synthetic

<400> SEQUENCE: 217

Thr Lys Gly Arg Asp Ala Phe Asp Ile
1               5

<210> SEQ ID NO 218
<211> LENGTH: 321
<212> TYPE: DNA
<213> ORGANISM: Artificial Sequence
<220> FEATURE:
<223> OTHER INFORMATION: Synthetic

<400> SEQUENCE: 218
gatattgtga tgacccagtc tccatcttcc gtgtctgcat ctgtaggaga cagagtcacc     60
atcacttgtc gggcgagtca gggtattagc agctggttag cctggtatca gcagaaacca    120
gggaaagccc ctaagctcct gatctatgct gcatccagtt tgcaaagtgg ggtcccatca    180
aggttcagcg gcagtggatc tgggacagat ttcactctca ccatcagcag cctgcagcct    240
gaagattttg caacttacta ttgtcaacag gctaacagtt tcccgtacac ttttggccag    300
gggaccaagc tggagatcaa a                                              321

<210> SEQ ID NO 219
<211> LENGTH: 107
<212> TYPE: PRT
<213> ORGANISM: Artificial Sequence
<220> FEATURE:
<223> OTHER INFORMATION: Synthetic

<400> SEQUENCE: 219

Asp Ile Val Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Tyr
                85                  90                  95

Thr Phe Gly Gln Gly Thr Lys Leu Glu Ile Lys
            100                 105

<210> SEQ ID NO 220
<211> LENGTH: 18
<212> TYPE: DNA
<213> ORGANISM: Artificial Sequence
<220> FEATURE:

<223> OTHER INFORMATION: Synthetic

<400> SEQUENCE: 220
cagggtatta gcagctgg                                           18

<210> SEQ ID NO 221
<211> LENGTH: 6
<212> TYPE: PRT
<213> ORGANISM: Artificial Sequence
<220> FEATURE:
<223> OTHER INFORMATION: Synthetic

<400> SEQUENCE: 221

Gln Gly Ile Ser Ser Trp
1               5

<210> SEQ ID NO 222
<211> LENGTH: 9
<212> TYPE: DNA
<213> ORGANISM: Artificial Sequence
<220> FEATURE:
<223> OTHER INFORMATION: Synthetic

<400> SEQUENCE: 222 gctgcatcc                                                      9

<210> SEQ ID NO 223
<211> LENGTH: 3
<212> TYPE: PRT
<213> ORGANISM: Artificial Sequence
<220> FEATURE:
<223> OTHER INFORMATION: Synthetic

<400> SEQUENCE: 223

Ala Ala Ser
1

<210> SEQ ID NO 224
<211> LENGTH: 27
<212> TYPE: DNA
<213> ORGANISM: Artificial Sequence
<220> FEATURE:
<223> OTHER INFORMATION: Synthetic

<400> SEQUENCE: 224
caacaggcta acagtttccc gtacact                                 27

<210> SEQ ID NO 225
<211> LENGTH: 9
<212> TYPE: PRT
<213> ORGANISM: Artificial Sequence
<220> FEATURE:
<223> OTHER INFORMATION: Synthetic

<400> SEQUENCE: 225

Gln Gln Ala Asn Ser Phe Pro Tyr Thr
1               5

<210> SEQ ID NO 226
<211> LENGTH: 378
<212> TYPE: DNA
<213> ORGANISM: Artificial Sequence
<220> FEATURE:
<223> OTHER INFORMATION: Synthetic

<400> SEQUENCE: 226

```
gaagtgcagc tggtggaatc tggaggagga ctggtgcagc tggaagatct ctgagactg      60 tcttgtgctg cttctggatt tatctttgat gattatgcta tgcattgggt gagacaggct     120
cctggaaagg gactggaatg ggtgtctgga atctcttgga attctggatc tatcggatat     180
gctgattctg tgaagggaag atttacaatc tctagagata tgctaagaa ttctctgtat      240 ctgcagatga attctctgag agctgaagat acagctctgt attattgtgc taaggatgga    300
ggatcttctt ggctgccttt tgtgtattat tatggaatgg atgtgtgggg acagggaaca    360
acagtgacag tgtcttct                                                   378
```

<210> SEQ ID NO 227
<211> LENGTH: 126
<212> TYPE: PRT
<213> ORGANISM: Artificial Sequence
<220> FEATURE:
<223> OTHER INFORMATION: Synthetic

<400> SEQUENCE: 227

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Ile Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Gly Gly Ser Ser Trp Leu Pro Phe Val Tyr Tyr Tyr Gly
            100                 105                 110

Met Asp Val Trp Gly Gln Gly Thr Thr Val Thr Val Ser Ser
        115                 120                 125
```

<210> SEQ ID NO 228
<211> LENGTH: 324
<212> TYPE: DNA
<213> ORGANISM: Artificial Sequence
<220> FEATURE:
<223> OTHER INFORMATION: Synthetic

<400> SEQUENCE: 228

```
gaaatcgtga tgacacagtc tcctgctaca ctgtctgtgt ctcctggaga aagagctaca      60
ctgtcttgta gagcttctca gtctatctct ctaatctgg cttggtatca gcagaagcct     120
ggacaggctc ctagactgct gatctatgga gcttctacaa gagctacagg aatccctgct    180
agattttctg gatctggatc tggaacagaa tttacactga caatctcttc tctgcagtct    240
gaagattttg ctgtgtatta ttgtcagcag tattcttctt ggcctcctta cattttgga    300 cagggaacaa agctggaaat caag                                            324
```

<210> SEQ ID NO 229
<211> LENGTH: 108
<212> TYPE: PRT
<213> ORGANISM: Artificial Sequence
<220> FEATURE:
<223> OTHER INFORMATION: Synthetic

<400> SEQUENCE: 229

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Ser Ser Trp Pro Pro
                85                  90                  95

Tyr Thr Phe Gly Gln Gly Thr Lys Leu Glu Ile Lys
            100                 105

<210> SEQ ID NO 230
<211> LENGTH: 348
<212> TYPE: DNA
<213> ORGANISM: Artificial Sequence
<220> FEATURE:
<223> OTHER INFORMATION: Synthetic

<400> SEQUENCE: 230
gaggtccagc tggtcgagtc aggaggaggc ctcgtccaac agggcgcag ccttcgactc    60 tcctgtgccg ccagtaggtt tactttcgat gactatgcca tgcactgggt ccggcaggcc   120
cctggtaagg gcttggagtg ggtgtccggt atctcctgga actccggacg tatcggttac   180
gccgacagcg tgaagggaag gttcactatc tctcgtgaca cgccaagaa ctccttgtat   240 ctgcaaatga acagcctccg ggccgaagac accgccttgt attactgtgc caagggtagg   300
gatagtttcg atatctgggg tcaaggcacc atggtgactg tgtcttca                348

<210> SEQ ID NO 231
<211> LENGTH: 116
<212> TYPE: PRT
<213> ORGANISM: Artificial Sequence
<220> FEATURE:
<223> OTHER INFORMATION: Synthetic

<400> SEQUENCE: 231

Glu Val Gln Leu Val Glu Ser Gly Gly Gly Leu Val Gln Pro Gly Arg
1               5                   10                  15

Ser Leu Arg Leu Ser Cys Ala Ala Ser Arg Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Arg Ile Gly Tyr Ala Asp Ser Val
50                  55                  60

Lys Gly Arg Phe Thr Ile Ser Arg Asp Asn Ala Glu Asn Ser Leu Phe
65                  70                  75                  80

Leu Gln Met Asn Gly Leu Arg Ala Glu Asp Thr Ala Leu Tyr Tyr Cys
                85                  90                  95

Ala Lys Gly Arg Asp Ser Phe Asp Ile Trp Gly Gln Gly Thr Met Val
            100                 105                 110

Thr Val Ser Ser
            115

<210> SEQ ID NO 232
<211> LENGTH: 321
<212> TYPE: DNA
<213> ORGANISM: Artificial Sequence
<220> FEATURE:
<223> OTHER INFORMATION: Synthetic

<400> SEQUENCE: 232

```
gacatacaga tgacccaaag cccaagcagc gttagcgctt ccgtaggcga cagggtgaca      60
attacatgca gagcctctca gggaatttct tcatggctgg catggtatca gcagaagccc     120
ggaaaagctc ccaagctgct gatatatggt gcctcctctc tccaaagcgg agtcccatca     180
cgcttctccg ggagtggctc tggtacagat tttactttga caatctctag ccttcagcct     240
gaagactttg ctacatacta ctgtcagcag gccaacagtt ttccttacac cttcggtcag     300
ggaactaaac tggaaattaa g                                               321
```

<210> SEQ ID NO 233
<211> LENGTH: 107
<212> TYPE: PRT
<213> ORGANISM: Artificial Sequence
<220> FEATURE:
<223> OTHER INFORMATION: Synthetic

<400> SEQUENCE: 233

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Tyr
                85                  90                  95

Thr Phe Gly Gln Gly Thr Lys Leu Glu Ile Lys
            100                 105

<210> SEQ ID NO 234
<211> LENGTH: 360
<212> TYPE: DNA
<213> ORGANISM: Artificial Sequence
<220> FEATURE:
<223> OTHER INFORMATION: Synthetic

<400> SEQUENCE: 234

```
caggtgcagc tggtgcagtc tggagctgaa gtgaagaagc ctggagcttc tgtgaaggtg      60
tcttgtaagg cttctggata cattaca tcttatgata tcatctgggt gagacaggct     120
acaggacagg gactggaatg gatgggatgg atgaatccta attctggaaa tacaggatat     180
gctcagaagt ttcagggaag agtgacaatg acaagaaata catctatctc tacagtgtat     240
atggaactgt cttctctgag atctgaagat acagctgtgt attattgtgc tagagattat     300
tcttctcatt attatggact ggatgtgtgg ggacagggaa caacagtgac agtgtcttct     360
```

<210> SEQ ID NO 235
<211> LENGTH: 120
<212> TYPE: PRT
<213> ORGANISM: Artificial Sequence
<220> FEATURE:
<223> OTHER INFORMATION: Synthetic

<400> SEQUENCE: 235

Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr Ser Tyr
            20                  25                  30

Asp Ile Ile Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Tyr Ser Ser His Tyr Tyr Gly Leu Asp Val Trp Gly Gln
            100                 105                 110

Gly Thr Thr Val Thr Val Ser Ser
        115                 120

<210> SEQ ID NO 236
<211> LENGTH: 321
<212> TYPE: DNA
<213> ORGANISM: Artificial Sequence
<220> FEATURE:
<223> OTHER INFORMATION: Synthetic

<400> SEQUENCE: 236
gatatccagc tgacacagtc tccttctttt ctgtctgctt ctgtgggaga tagagtgaca    60
atcacatgta gagcttctca ggatatctct aattatctgg cttggtatca gcagaagcct   120
ggaaaggctc ctaagctgct gatctatgtg gcttctacac tgcagtctgg agtgccttct   180
agattttctg gatctggatc tggaacagaa tttacactga caatctcttc tctgcagcct   240
gaagattttg ctacatatta ttgtcagcag tttaattctt atcctctgac atttggagga   300
ggaacaaagg tggaaatcaa g                                             321

<210> SEQ ID NO 237
<211> LENGTH: 107
<212> TYPE: PRT
<213> ORGANISM: Artificial Sequence
<220> FEATURE:
<223> OTHER INFORMATION: Synthetic

<400> SEQUENCE: 237

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Ala Trp Tyr Gln Gln Lys Pro Gly Lys Ala Pro Lys Leu Leu Ile
        35                  40                  45

Tyr Val Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

```
Thr Phe Gly Gly Gly Thr Lys Val Glu Ile Lys
            100                 105
```

<210> SEQ ID NO 238
<211> LENGTH: 349
<212> TYPE: DNA
<213> ORGANISM: Artificial Sequence
<220> FEATURE:
<223> OTHER INFORMATION: Synthetic

<400> SEQUENCE: 238

```
gaagtgcagc tggtggagtc tgggggaggc ttggtacagc ctggcaggtc cctgagactc      60
tcctgtgcag cctctggatt cacctttgat gattatgccc tgcactgggt ccggcaagct     120
ccagggaagg gcctggagtg ggtctcaggt gttagttgga atggtggtag aataggctat     180
gcggactctg tgaaaggccg attcaccatc tccagagaca cgccaagaa ctccctcttt      240
ctgcaaatga acagtctgag agttgaggac acggccttgt attattgtgc aaaaggccgg     300
gatgcttttg atatctgggg ccaagggaca ttggtcaccg tctcttcag                 349
```

<210> SEQ ID NO 239
<211> LENGTH: 116
<212> TYPE: PRT
<213> ORGANISM: Artificial Sequence
<220> FEATURE:
<223> OTHER INFORMATION: Synthetic

<400> SEQUENCE: 239

```
Glu Val Gln Leu Val Glu Ser Gly Gly Gly Leu Val Gln Pro Gly Arg
1               5                   10                  15
Ser Leu Arg Leu Ser Cys Ala Ala Ser Gly Phe Thr Phe Asp Asp Tyr
            20                  25                  30
Ala Leu His Trp Val Arg Gln Ala Pro Gly Lys Gly Leu Glu Trp Val
        35                  40                  45
Ser Gly Val Ser Trp Asn Gly Gly Arg Ile Gly Tyr Ala Asp Ser Val
    50                  55                  60
Lys Gly Arg Phe Thr Ile Ser Arg Asp Asn Ala Lys Asn Ser Leu Phe
65                  70                  75                  80
Leu Gln Met Asn Ser Leu Arg Val Glu Asp Thr Ala Leu Tyr Tyr Cys
                85                  90                  95
Ala Lys Gly Arg Asp Ala Phe Asp Ile Trp Gly Gln Gly Thr Met Val
            100                 105                 110
Thr Val Ser Ser
        115
```

<210> SEQ ID NO 240
<211> LENGTH: 348
<212> TYPE: DNA
<213> ORGANISM: Artificial Sequence
<220> FEATURE:
<223> OTHER INFORMATION: Synthetic

<400> SEQUENCE: 240

```
gaagtgcagc tggtggaatc tggaggagga ctggtgcagc ctggaagatc tctgagactg      60
tcttgtgctg cttctggatt tacatttgat gattatgcta tgcattgggt gagacaggct     120
cctggaaagg gactggaatg ggtgtctgga gtgtcttgga atggaggaag aatcggatat     180
gctgattctg tgaagggaag atttacaatc tctagagata tgctaagaa ttctctgtat      240
ctgcagatga attctctgag agctgaagat acagctctgt attattgtgc taagggaaga     300
```

```
gatgcttttg atatctgggg acagggaaca atggtgacag tgtcttct                    348
```

<210> SEQ ID NO 241
<211> LENGTH: 116
<212> TYPE: PRT
<213> ORGANISM: Artificial Sequence
<220> FEATURE:
<223> OTHER INFORMATION: Synthetic

<400> SEQUENCE: 241

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Val Ser Trp Asn Gly Arg Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Gly Arg Asp Ala Phe Asp Ile Trp Gly Gln Gly Thr Met Val
            100                 105                 110

Thr Val Ser Ser
        115
```

<210> SEQ ID NO 242
<211> LENGTH: 330
<212> TYPE: PRT
<213> ORGANISM: Artificial Sequence
<220> FEATURE:
<223> OTHER INFORMATION: Synthetic

<400> SEQUENCE: 242

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175
```

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 243
<211> LENGTH: 327
<212> TYPE: PRT
<213> ORGANISM: Artificial Sequence
<220> FEATURE:
<223> OTHER INFORMATION: Synthetic

<400> SEQUENCE: 243

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

```
Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 244
<211> LENGTH: 327
<212> TYPE: PRT
<213> ORGANISM: Artificial Sequence
<220> FEATURE:
<223> OTHER INFORMATION: Synthetic

<400> SEQUENCE: 244

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240
```

```
Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 245
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)..(6)
<223> OTHER INFORMATION: Xaa = Any Amino Acid

<400> SEQUENCE: 245

```
Xaa Xaa Xaa Xaa Xaa Xaa
1               5
```

<210> SEQ ID NO 246
<211> LENGTH: 3
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)..(3)
<223> OTHER INFORMATION: Xaa = Any Amino Acid

<400> SEQUENCE: 246

```
Xaa Xaa Xaa
1
```

<210> SEQ ID NO 247
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)..(10)
<223> OTHER INFORMATION: Xaa = Any Amino Acid

<400> SEQUENCE: 247

```
Xaa Xaa Xaa Xaa Xaa Xaa Xaa Xaa Xaa Xaa
1               5                   10
```

<210> SEQ ID NO 248
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)..(8)

```
<223> OTHER INFORMATION: Xaa = Any Amino Acid

<400> SEQUENCE: 248

Xaa Xaa Xaa Xaa Xaa Xaa Xaa Xaa
1               5

<210> SEQ ID NO 249
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)..(8)
<223> OTHER INFORMATION: Xaa = Any Amino Acid

<400> SEQUENCE: 249

Xaa Xaa Xaa Xaa Xaa Xaa Xaa Xaa
1               5

<210> SEQ ID NO 250
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)..(19)
<223> OTHER INFORMATION: Xaa = Any Amino Acid

<400> SEQUENCE: 250

Xaa Xaa Xaa Xaa Xaa Xaa Xaa Xaa Xaa Xaa Xaa Xaa Xaa Xaa Xaa
1               5                   10                  15

Xaa Xaa Xaa

<210> SEQ ID NO 251
<211> LENGTH: 311
<212> TYPE: PRT
<213> ORGANISM: Macaca Fascicularis

<400> SEQUENCE: 251

Ala Pro Gly Gly Cys Pro Ala Gln Glu Val Ala Arg Gly Val Leu Thr
1               5                   10                  15

Ser Leu Pro Gly Asp Ser Val Thr Leu Thr Cys Pro Gly Gly Glu Pro
                20                  25                  30

Glu Asp Asn Ala Thr Val His Trp Val Leu Arg Lys Pro Ala Val Gly
            35                  40                  45

Ser His Leu Ser Arg Trp Ala Gly Val Gly Arg Leu Leu Leu Arg
        50                  55                  60

Ser Val Gln Leu His Asp Ser Gly Asn Tyr Ser Cys Tyr Arg Ala Gly
65                  70                  75                  80

Arg Pro Ala Gly Thr Val His Leu Leu Val Asp Val Pro Pro Glu Glu
                85                  90                  95

Pro Gln Leu Ser Cys Phe Arg Lys Ser Pro Leu Ser Asn Val Ala Cys
            100                 105                 110

Glu Trp Gly Pro Arg Ser Thr Pro Ser Pro Thr Thr Lys Ala Val Leu
        115                 120                 125

Leu Val Arg Lys Phe Gln Asn Ser Pro Ala Glu Asp Phe Gln Glu Pro
    130                 135                 140

Cys Gln Tyr Ser Gln Glu Ser Gln Lys Phe Ser Cys Gln Leu Ala Val
```

-continued

```
145                 150                 155                 160
Pro Glu Gly Asp Ser Ser Phe Tyr Ile Val Ser Met Cys Val Ala Ser
                165                 170                 175

Ser Val Gly Ser Lys Leu Ser Lys Thr Gln Thr Phe Gln Gly Cys Gly
                180                 185                 190

Ile Leu Gln Pro Asp Pro Pro Ala Asn Ile Thr Val Thr Ala Val Ala
                195                 200                 205

Arg Asn Pro Arg Trp Leu Ser Val Thr Trp Gln Asp Pro His Ser Trp
    210                 215                 220

Asn Ser Ser Phe Tyr Arg Leu Arg Phe Glu Leu Arg Tyr Arg Ala Glu
225                 230                 235                 240

Arg Ser Lys Thr Phe Thr Thr Trp Met Val Lys Asp Leu Gln His His
                245                 250                 255

Cys Val Ile His Asp Ala Trp Ser Gly Leu Arg His Val Val Gln Leu
                260                 265                 270

Arg Ala Gln Glu Glu Phe Gly Gln Gly Glu Trp Ser Glu Trp Ser Pro
    275                 280                 285

Glu Ala Met Gly Thr Pro Trp Thr Glu Ser Arg Ser Pro Pro Ala Glu
    290                 295                 300

Asn Glu Val Ser Thr Pro Thr
305                 310
```

HIGH AFFINITY ANTIBODIES TO HUMAN IL-6 RECEPTOR

FIELD OF THE INVENTION

The present invention related to human antibodies and antibody fragments specific for human interleukin 6 receptor (hIL-6R) (extracellular domain hIL6-R SEQ ID NO:1), pharmaceutical compositions, and therapeutic methods thereof.

Statement of Related Art

Interleukin-6 (IL-6) is a pleiotropic cytokine produced by immune and non-immune cells that plays a crucial role in regulation of immune response, acute-phase reactions, and hematopoiesis. It binds to soluble and cell membrane bound IL-6R (α chain) forming a binary complex and this complex is able to interact with cell membrane bound gp130 (β chain), induces formation of signaling complex comprising two each of IL-6, IL-6R, and gp130.

Antibodies to hIL-6R are described in U.S. Pat. Nos. 5,670,373, 5,795,965, 5,817,790, 6,410,691, and EP 409 60761. Therapeutic methods are described in U.S. Pat. Nos. 5,888,510 and 6,723,319.

BRIEF SUMMARY OF THE INVENTION

In a first aspect, the invention provides human antibodies, preferably recombinant human antibodies that specifically bind human interleukin-6 receptor (hIL-6R). These antibodies are characterized by binding to hIL-6R with high affinity and slow dissociation kinetics and by the ability to neutralize IL-6 activity. The antibodies can be full-length (for example, an IgG1 or IgG4 antibody) or may comprise only an antigen-binding portion (for example, a Fab, F(ab')$_2$ or scFv fragment), and may be modified to effect functionality, e.g., to eliminate residual effector functions (Reddy et al. (2000) J. Immunol. 164:1925-1933). In a preferred embodiment, the invention provides an antibody or antigen-binding fragment thereof, which binds human IL-6 receptor (SEQ ID NO:1) with a $K_D$ of about 500 pM or less, as measured by surface plasmon resonance. In a more specific embodiment, the antibody or antigen-binding fragment has a $K_D$ of less than 300 pM, or less than 200 pM, or even less than 100 pM. In various embodiments, the antibody or antigen-binding fragment thereof blocks hIL-6 activity with an $IC_{50}$ of 250 pM or less, as measured by luciferase bioassay. In more specific embodiments, the antibody or antigen-binding fragment thereof exhibits an $IC_{50}$ of 150 pM or less.

In related aspects, the antibody or antigen-binding fragment of the invention binds hIL-6R with an affinity at least 2-fold higher than it binds monkey IL-6R. In more preferred embodiments, the antibody or antigen-binding fragment binds hIL-6R protein (SEQ ID NO:1) with an affinity that is up to about 3-fold higher relative to its binding to monkey IL-6R (*Macaca fascicularis* extracellular domain shown in SEQ ID NO:251).

In one embodiment, the antibody or antigen-binding portion of the antibody of the invention comprises a heavy chain variable region (HCVR) selected from the group consisting of SEQ ID NO:3, 227, 19, 231, 35, 51, 67, 83, 99, 115, 131, 147, 239, 241, 163, 179, 235, 195 and 211, or substantially similar sequence thereof. In a more specific embodiment, the antibody or antigen-binding fragment thereof further comprises a light chain variable region (LCVR) selected from the group consisting of SEQ ID NO: 11, 229, 27, 233, 43, 59, 75, 91, 107, 123, 139, 155, 171, 187, 203 and 219, or a substantially similar sequence thereof. In specific embodiments, the antibody or antigen-binding fragment thereof comprise HCVR/LCVR pairs selected from the group consisting of SEQ ID NO:3/11; 227/229; 19/27; 231/233; 35/43; 51/59; 67/75; 83/91; 99/107; 115/123; 131/139; 147/155; 239/155; 241; 155; 163/171; 179/187; 235/237; 195/203; and 211/219, or substantially similar sequences thereof.

In a second aspect, the invention provides isolated nucleic acid molecules that encode an antibody or antigen-binding fragment of an antibody of the invention. In one embodiment, the nucleic acid molecule of the invention encodes an antibody or fragment thereof comprising an HCVR as described above. In specific embodiments, the nucleic acid molecule encoding the HCVR is selected from the group consisting of SEQ ID NO:2, 226, 18, 230, 34, 50, 66, 82, 98, 114, 130, 146, 238, 240, 162, 178, 234, 194 and 210, or a substantially identical sequence thereof. In a related aspect, the invention provides an isolated nucleic acid molecule encoding an LCVR as described above. In specific embodiments, the nucleic acid molecule encoding the LCVR is a nucleotide sequence selected from the group consisting of SEQ ID NO: 10, 228, 26, 232, 42, 58, 74, 90, 106, 122, 138, 154, 170, 186, 236, 202 and 218, or a substantially identical sequence thereof.

In a third aspect, the invention features an antibody or antigen-binding fragment, comprising a heavy chain complementary determining region 3 (CDR3) domain and a light chain CDR3 domain, wherein the heavy chain CDR3 domain comprises an amino acid sequence of the formula $X^1-X^2-X^3-X^4-X^5-X^6-X^7-X^8-X^9-X^{10}-X^{11}-X^{12}-X^{13}-X^{14}-X^{15}-X^{16}-X^{17}-X^{18}-X^{19}$ (SEQ ID NO:247) wherein $X^1$=Ala, $X^2$=Lys, $X^3$=Gly, $X^4$=Arg, $X^5$=Asp, $X^6$=Ser or Ala, $X^7$=Phe, $X^8$=Asp; $X^9$=Ile, $X^{10}$=Pro or absent, $X^{11}$=Phe or absent, $X^{12}$=Val or absent, $X^{13}$=Tyr or absent, $X^{14}$=Tyr or absent, $X^{15}$=Tyr or absent, $X^{16}$=Gly or absent, $X^{17}$=Met or absent, $X^{18}$=Asp or absent, and $X^{19}$=Val or absent; and the light chain CDR3 domain comprises an amino acid sequence of the formula $X^1-X^2-X^3-X^4-X^5-X^6-X^7-X^8-X^9$ (SEQ ID NO:250) wherein $X^1$=Gln, $X^2$=Gln or His, $X^3$=Ala, $X^4$=Asn or Tyr, $X^5$=Ser, $X^6$=Phe, $X^7$=Pro, $X^8$=Pro, and $X^9$=Thr.

In a more specific embodiment, the antibody or antigen-binding fragment further comprises a heavy chain CDR1 domain comprising an amino acid sequence of the formula $X^1-X^2-X^3-X^4-X^5-X^6-X^7-X^8$ (SEQ ID NO:245) wherein $X^1$=Gly or Arg, $X^2$=Phe, $X^3$=Thr, $X^4$=Phe, $X^5$=Asp, $X^6$=Asp, $X^7$=Tyr, and $X^8$=Ala;

a heavy chain CDR2 domain comprising an amino acid sequence of the formula $X^1-X^2-X^3-X^4-X^5-X^6-X^7-X^8$ (SEQ ID NO:246) wherein $X^1$=Ile or Val, $X^2$=Ser, $X^3$=Trp, $X^4$=Asn, $X^5$=Ser, $X^6$=Gly, $X^7$=Ser, and $X^8$=Ile;

light chain CDR1 domain comprising an amino acid sequence of the formula $X^1-X^2-X^3—X^4-X^5-X^6-X^7-X^8$ (SEQ ID NO:248), wherein $X^1$=Gln, $X^2$=Gly, $X^3$=Ile, $X^4$=Ser, $X^5$=Ser, and $X^6$=Trp; and a light chain CDR2 domain comprising an amino acid sequence of the formula $X^1-X^2-X^3$ (SEQ ID NO:249), wherein $X^1$=Gly or Ala, $X^2$=Ala, and $X^3$=Ser.

In a fourth aspect, the invention features an antibody or antigen-binding fragment, comprising:

a heavy chain CDR3 domain selected from the group consisting of SEQ ID NO: 25, 153, 9, 185, 41, 57, 73, 89, 105, 121, 137, 169, 201 and 217; and a light chain CDR3 domain selected from the group consisting of SEQ ID NO:33, 161, 17, 193, 49, 65, 81, 97, 113, 129, 145, 177, 209 and 225.

In a more specific embodiment, the antibody or antigen-binding fragment further comprises:

a heavy chain CDR1 domain selected from the group consisting of SEQ ID NO: 21, 149, 5, 181, 37, 53, 69, 85, 101, 117, 133, 165, 197, and 213;

a heavy chain CDR2 domain selected from the group consisting of SEQ ID NO: 23, 151, 7, 183, 39, 55, 71, 87, 103, 119, 135, 167, 199 and 215;

a light chain CDR1 domain selected from the group consisting of SEQ ID NO: 29, 157, 13, 189, 45, 61, 77, 93, 109, 125, 141, 173, 205 and 221; and a light chain CDR2 domain selected from the group consisting of SEQ ID NO: 31, 159, 15, 191, 47, 63, 79, 95, 111, 127, 143, 175, 207 and 223.**

In specific embodiments, the antigen or antigen-binding fragment comprises heavy chain CDR sequences SEQ ID NO:21, 23, 25 and light chain CDR sequences SEQ ID NO:29, 31, 33; heavy chain CDR sequences SEQ ID NO:149, 151, 153 and light chain CDR sequences SEQ ID NO:157, 159, 161; heavy chain CDR sequences SEQ ID NO:5, 7, 9 and light chain SEQ ID NO: 13, 15, 17; and heavy chain CDR sequences SEQ ID NO: 181. 183, 185 and light chain CDR sequences SEQ ID NO:189, 191, and 193.

In a fifth aspect, the invention features isolated nucleic acid molecules encoding an antibody or antigen-binding fragments of the invention, wherein the antibody or fragment thereof comprises a heavy chain CDR3 domain encoded by a nucleotide sequence selected from the group consisting of SEQ ID NO:24, 152, 8, 184, 40, 56, 72, 88, 104, 120, 136, 168, 200 and 216; and a light chain CDR3 domain encoded by a nucleotide sequence selected from the group consisting of SEQ ID NO:32, 160, 16, 192, 48, 64, 80, 96, 112, 128, 144, 176, 208 and 224; as well as substantially identical nucleic acid sequences thereof.

In a more specific embodiment, isolated nucleic acid molecules are provided encoding an antibody or antigen-binding fragment of the invention, wherein the antibody or fragment thereof comprises a heavy chain CDR1 encoded by a nucleotide sequence selected from the group consisting of SEQ ID NO:20, 148, 4, 180, 36, 52, 68, 84, 100, 116, 132, 164, 196 and 212;

a heavy chain CDR2 domain encoded by a nucleotide sequence selected from the group consisting of SEQ ID NO:22, 150, 6, 182, 38, 54, 70, 86, 102, 118, 134, 166, 198 and 214;

a light chain CDR1 domain encoded by a nucleotide sequence selected from the group consisting of SEQ ID NO:28, 156, 12, 188, 44, 60, 76, 92, 108, 124, 140, 172, 204 and 220; and a light chain CDR2 domain encoded by a nucleotide sequence selected from the group consisting of SEQ ID NO:30, 158, 14, 190, 46, 62, 78, 94, 110, 126, 142, 174, 206 and 222; as well as substantially identical nucleic acid sequences thereof.

The invention encompasses anti-hIL-6R antibodies or antigen-binding fragments thereof having a modified glycosylation pattern. In some applications, modification to remove undesirable glycosylation sites may be useful, or an antibody lacking a fucose moiety on an oligosaccharide chain, for example, to increase antibody-dependent cellular cytotoxicity (ADCC) (see Shield et al. (2002) JBC 277: 26733). In other applications, modification of a galactosylation can be made in order to modify complement-dependent cytotoxicity (CDC).

In further aspects, the invention provides recombinant expression vectors carrying the nucleic acid molecules of the invention, and host cells into which such vectors have been introduced, as are methods of making the antibodies or antigen-binding fragments of the invention obtained by culturing the host cells of the invention. The host cell may be a prokaryotic or eukaryotic cell, preferably the host cell is an *E. coli* cell or a mammalian cell, such as a CHO cell.

In a further aspect, the invention features a pharmaceutical composition comprising a human antibody or antigen-binding fragment of an antibody which specifically binds hIL-6R and a pharmaceutically acceptable carrier.

In further aspects, the invention features methods for inhibiting human IL-6 activity using an antibody, or antigen-binding portion thereof, of the invention. In one embodiment, the invention encompasses a therapeutic method comprising administering an antibody of the invention, or a fragment thereof, to a human subject suffering from a disorder which is treated or ameliorated by inhibition of IL-6 activity. The disorder can be, for example, arthritis, including chronic rheumatoid arthritis; inflammatory bowel diseases, including Crohn's disease and ulcerative colitis; systemic lupus erythematosus; and inflammatory diseases.

Other objects and advantages will become apparent from a review of the ensuing detailed description.

DETAILED DESCRIPTION

Before the present methods are described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to describe in their entirety.

The term "human IL6R" (hIL-6R), as used herein, is intended to refer to a human cytokine receptor that specifically binds interleukin-6 (IL-6). The extracellular domain of hIL-6R is shown in SEQ ID NO:1.

The term "antibody", as used herein, is intended to refer to immunoglobulin molecules comprising four polypeptide chains, two heavy (H) chains and two light (L) chains inter-connected by disulfide bonds. Each heavy chain comprises a heavy chain variable region (abbreviated herein as HCVR or VH) and a heavy chain constant region. The heavy chain constant region comprises three domains, CH1, CH2 and CH3. Each light chain comprises a light chain variable region (abbreviated herein as LCVR or VL) and a light chain constant region. The light chain constant region is comprised of one domain (CL1). The VH and VL regions can be further subdivided into regions of hypervariability, termed complementary determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, and FR4.

The term "antigen-binding portion" of an antibody (or simply "antibody portion" or "antibody fragment"), as used herein, refers to one or more fragments of an antibody that retain the ability to specifically bind to an antigen (e.g., hIL-6R). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL1 and CH1 domains; (ii) a F(ab')$_2$ fragment, a bivalent fragment comprising two F(ab)' fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al. (1989) Nature 241:544-546), which consists of a VH domain; and (vi) an isolated complementary determining region (CDR). Furthermore, although the two domains of the Fv fragment, VL and VH, are coded for by separate genes, they can be joined, using recombinant methods, by a synthetic linker that enables them to be made as a single contiguous chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. Other forms of single chain antibodies, such as diabodies, are also encompassed (see e.g., Holliger et al. (1993) Proc. Natl. Acad Sci. USA 90:6444-6448).

A "neutralizing" or "blocking" antibody, as used herein, is intended to refer to an antibody whose binding to hIL-6R results in inhibition of the biological activity of hIL-6. This inhibition of the biological activity of hIL-6 can be assessed by measuring one or more indicators of hIL-6 biological activity known to the art, such as hIL-6-induced cellular activation and hIL-6 binding to hIL-6R (see examples below).

A "CDR" or complementary determining region is a region of hypervariability interspersed within regions that are more conserved, termed "framework regions" (FR). In different embodiments of the anti-hiL-6R antibody or fragment of the invention, the FRs may be identical to the human germline sequences, or may be naturally or artificially modified. A group of CDRs may be defined as an amino acid consensus sequence; for example, in one embodiment, the anti-hIL-6R antibody or antigen-binding fragment of the invention may be described as comprising a heavy chain CDR3 domain comprising an amino acid sequence of the formula $X^1$-$X^2$-$X^3$-$X^4$-$X^5$-$X^6$-$X^7$-$x^8$-$X^9$-$X^{10}$-$X^{11}$-$X^{12}$-$X^{13}$-$X^{14}$-$X^{15}$-$X^{16}$-$X^{17}$-$X^{18}$-$X^{19}$ (SEQ ID NO:247) wherein $X^1$=Ala, $X^2$=Lys, $X^3$=Gly, $X^4$=Arg, $X^5$=Asp, $X^6$=Ser or Ala, $X^7$=Phe, $X^8$=Asp; $X^9$=Ile, $X^{10}$=Pro or absent, $X^{11}$=Phe or absent, $X^{12}$=Val or absent, $X^{13}$=Tyr or absent, $X^{14}$=Tyr or absent, $X^{15}$=Tyr or absent, $X^{16}$=Gly or absent, $X^{17}$=Met or absent, $X^{18}$=Asp or absent, and $X^{19}$=Val or absent; and a light chain CDR3 domain comprising an amino acid sequence of the formula $X^1$-$X^2$-$X^3$-$X^4$-$X^5$-$X^6$-$X^8$-$X^9$ (SEQ ID NO:250) wherein $X^1$=Gln, $X^2$=Gln or His, $X^3$=Ala, $X^4$=Asn or Tyr, $X^5$=Ser, $X^6$=Phe, $X^7$=Pro, $X^8$=Pro, and $X^9$=Thr.

The term "surface plasmon resonance", as used herein, refers to an optical phenomenon that allows for the analysis of real-time interactions by detection of alterations in protein concentrations within a biosensor matrix, for example using the BIAcore™ system (Pharmacia Biosensor AB).

The term "epitope" is an antigenic determinant that interacts with a specific antigen binding site in the variable region of an antibody molecule known as a paratope. A single antigen may have more than one epitope. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443 45, herein incorporated by reference. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially blastp or tblastn, using default parameters. See, e.g., Altschul et al. (1990) J. Mol. Biol. 215: 403 410 and Altschul et al. (1997) Nucleic Acids Res. 25:3389 402, each of which is herein incorporated by reference.

Preparation of Human Antibodies

Methods for generating human antibodies include, for example, VelocImmune™ (Regeneron Pharmaceuticals), XenoMouse™ technology (Green et al. (1994) Nature Genetics 7:13-21; Abgenix), the "minilocus" approach, and phage display (and see, for example, U.S. Pat. Nos. 5,545,807, 6,787,637). The VelocImmune™ technology (U.S. Pat. No. 6,596,541) encompasses a method of generating a high specificity fully human antibody to a select antigen. This technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody. In specific embodiment, the cell is a CHO cell.

Antibodies may be therapeutically useful in blocking a ligand-receptor interaction or inhibiting receptor component interaction, rather than by killing cells through fixation of complement (complement-dependent cytotoxicity)(CDC) and participation antibody-dependent cell-mediated cytotoxicity (ADCC) The constant region of an antibody is important in the ability of an antibody to fix complement and mediate cell-dependent cytotoxicity. Thus, the isotype of an antibody may be selected on the basis of whether it is desirable for the antibody to mediate cytotoxicity.

Human immunoglobulins can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via interchain disulfide bonds and a molecule of about 75-80 kDa is formed composed of a covalently coupled light and heavy chain (half-antibody). These forms have been extremely difficult to separate, even after affinity purification. The frequency of appearance of the second form in various intact IgG isotypes is due to, but not limited to, structural differences associated with the hinge region isotype of the antibody. In fact, a single amino acid substitution in the hinge region of the human IgG4 hinge can significantly reduce the appearance of the second form (Angal et al. (1993) Molecular Immunology 30: 105) to levels typically observed using a human IgG1 hinge. The instant invention encompasses antibodies having one or more mutations in the hinge, CH2 or CH3 region which may be desirable, for example, in production, to improve the yield of the desired antibody form.

Antibodies of the invention are preferably prepared with the use of VelocImmune™ technology. A transgenic mouse in which the endogenous immunoglobulin heavy and light chain variable regions are replaced with the corresponding human variable regions is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable domains of the light and heavy chains may be isolated directly from antigen-specific lymphocytes.

In one embodiment, the transgenic mouse comprises up to 18 functional human variable heavy chain genes and 12 functional human variable kappa light chain genes. In another embodiment, the transgenic mouse comprises up to 39 human variable heavy chain genes and 30 human variable kappa light chain genes. In yet another embodiment, the transgenic mouse comprises up to 80 human variable heavy chain genes and 40 human variable kappa light chain genes.

In general, the antibodies of the instant invention possess very high affinities, typically possessing $K_D$s of from about $10^{-9}$ through about $10^{-12}$ M, when measured by binding to antigen either immobilized on solid phase or in solution phase.

Initially, high affinity chimeric antibodies are isolated having a human variable region and a mouse constant region. As described below, the antibodies are characterized and selected for desirable characteristics, including binding affinity to hIL-6R, ability to block hIL-6 binding to hIL-6R, and/or selectivity for the human protein. The mouse constant regions are replaced with a desired human constant region to generate the fully human antibody of the invention, for example wild-type or modified IgG4 or IgG1 (for example, SEQ ID NO:242, 243, and 244). While the constant region selected may vary according to specific use, high affinity antigen-binding and target specificity characteristics reside in the variable region.

Epitope Mapping and Related Technologies

To screen for antibodies which bind to a particular epitope, a routine cross-blocking assay such as that described in *Antibodies: A Laboratory Manual* 1988 Cold Spring Harbor Laboratory, Harlow and Lane, eds. (herein specifically incorporated by reference in its entirety) can be performed. Other methods include alanine scanning mutants, peptide blots (Reineke (2004) Methods Mol Biol 248:443-63), or peptide cleavage analysis as described in the examples below. In addition, methods such as epitope excision, epitope extraction and chemical modification of antigens can be employed (Tomer (2000) Protein Science: 9: 487-496).

Modification-Assisted Profiling (MAP), also known as Antigen Structure-based Antibody Profiling (ASAP) is a method that categorizes large numbers of monoclonal antibodies (mAbs) directed against the same antigen according to the similarities of the binding profile of each antibody to chemically or enzymatically modified antigen surfaces (US Patent Application Publication No. 2004/0101920, herein specifically incorporated by reference in its entirety). Each category may reflect a unique epitope either distinctly different from or partially overlapping with an epitope represented by another category. This technology allows rapid filtering of genetically identical antibodies, such that characterization can be focused on genetically distinct antibodies. When applied to hybridoma screening, MAP may facilitate identification of rare hybridoma clones with desired characteristics. MAP may be used to sort the hIL-6R antibodies of the invention into groups of antibodies binding different epitopes.

Agents useful for altering the structure of the immobilized antigen are enzymes, such as, for example proteolytic enzymes and chemical agents. The antigen protein may be immobilized on either biosensor chip surfaces or polystyrene beads. The latter can be processed with, for example, an assay such as a multiplex Luminex™ detection assay (Luminex Corp., TX). Because of the capacity of Luminex™ to handle multiplex analysis with up to 100 different types of beads, Luminex™ provides almost unlimited antigen surfaces with various modifications, resulting in improved resolution in antibody epitope profiling over a biosensor assay.

Therapeutic Administration and Formulations

The administration of therapeutic entities in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, Pa., 1975), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Powell et al. PDA (1998) J Pharm Sci Technol. 52:238-311 and the citations therein for additional information related to excipients and carriers well known to pharmaceutical chemists.

Examples

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1. Generation of Human Antibodies to Human IL-6 Receptor

Immunization of rodents can be done by any methods known in the art (see, for example, Harlow and Lane (1988) supra; Malik and Lillehoj, Antibody techniques: Academic Press, 1994, CA). In a preferred embodiment, hIL-6R antigen is administered directly to mice which comprise DNA loci encoding both human Ig heavy chain variable region and Kappa light chain variable region (VelocImmune™, Regeneron Pharmaceuticals, Inc.; U.S. Pat. No. 6,596,541), with an adjuvant to stimulate the immune response. Such an adjuvant includes complete and incomplete Freund's adjuvant, MPL+TDM adjuvant system (Sigma), or R1131 (muramyl dipeptides) (see O'Hagan, Vaccine Adjuvant, by Human Press, 2000, NJ). Such an adjuvant can prevent rapid dispersal of polypeptide by sequestering the antigen in a local depot, and may contain factors that can stimulate host immune response. In one embodiment, hIL-6R is administered indirectly as DNA plasmid that contains hIL-6R gene and expresses hIL-6R using the host cellular protein expression machinery to produce antigen polypeptide in vivo. In both approaches, the immunization schedule requires several administrations spaced by a few weeks. The antibody immune response is monitored by standard antigen-specific immunoassay. When animals reached their maximum immune response, the antibody expressing B cells were harvested and fused with mouse myeloma cells to preserve their viability, forming hybridoma cells. To select functionally desirable monoclonal antibodies, conditioned media of the hybridoma cells or transfected cells were screened for specificity, antigen-binding affinity, and potency in blocking hIL-6 binding to hIL-6R (described below).

Example 2. Anti-hIL6R Antibodies Generated Via Direct Isolation of Splenocytes

DNA encoding VH and VL domains may be isolated directly from a single antigen positive B cell. Briefly, the hIL-6Rα immunized transgenic mouse was terminated and splenocytes were harvested. Red blood cells were removed by lysis followed by pelleting the harvested splenocytes. Resuspended splenocytes were first incubated with a cocktail of human IgG, FITC-anti-mFc, and biotin-IL6Ra for 1 hour. The stained cells were washed twice with PBS, then stained with a cocktail of human and rat IgG, APC-anti-mIgM, and SA-PE for one hour. The stained cells were washed once with PBS and were analyzed by flow cytometry on a MoFlo (Cytomation). Each IgG positive, IgM negative, and antigen positive B cell was sorted and plated into a separate well on a 96-well plate. RT-PCR of antibody genes from these B cells was performed according to a method described by Wang et al. (2000) (J Immunol Methods 244:217-225). Briefly, cDNAs for each single B cell were synthesized via RT-PCR. Each resulting RT product was then split and transferred into two corresponding wells on two 96-well plates. One set of the resulting RT products was first amplified by PCR using a 5' degenerate primer specific for human IgG heavy chain variable region leader sequence and a 3' primer specific for mouse heavy chain constant region, to form an amplicon. The amplicon was then amplified again by PCR using a 5' degenerate primer set specific for framework 1 of human IgG heavy chain variable region sequence and a nested 3' primer specific for mouse heavy chain constant region. The other set of the resulting RT products was first amplified by PCR using a 5' degenerate primer specific for human kappa light chain variable region leader sequence and a 3' primer specific for mouse kappa light chain constant region to form an amplicon. The amplicon was then amplified again by PCR using a 5' degenerate primer set specific for framework 1 of human kappa light chain variable region sequence and a nested 3' primer specific for mouse kappa light chain constant region. The heavy chain and light chain PCR products were cloned into Sap I-linearized antibody vectors containing IgG1 heavy chain constant region and kappa light chain constant region, respectively. The heavy chain plasmid has a lox2272 site and a lox511 site flanking the heavy chain expression cassettes. In addition, immediately downstream of the lox2272 in the heavy chain plasmid there is a hygromycin-resistance gene that lacks a promoter and an initiating ATG. The hygromycin-resistance gene is also transcriptionally linked to a downstream eGFP gene via an IRES sequence. The light chain plasmid has a loxP site and lox2272 site flanking the light chain expression cassette. In addition, The light chain plasmid has a SV40 promoter immediately before an ATG at the lox2272 site, such that upon integration into an appropriate host cell the lox2272-proximal SV40 promoter and initiating ATG from the light chain plasmid is brought adjacent to the hygromycin-resistance gene in the heavy chain plasmid in the proper reading frame to allow transcription and translation of the hygromycin-resistance and eGFP genes. Purified recombinant plasmids having a heavy chain variable region sequence and plasmids having a light chain variable region sequence from the same B cell were then combined and transfected, together with a plasmid that expresses the Cre recombinase, into a modified CHO host cell line. The modified CHO host cell line contains, from 5' to 3', a loxP site, an eCFP, a lox2272 site, DsRed, and a lox511 site at a transcriptionally active locus. Consequently, the host CHO cell can be isolated by flow cytometry as a blue-positive, red-positive, and green-negative cell. When recombinant plasmids expressing heavy chain and light chain genes are transfected together with a plasmid expressing the Cre recombinase, site-specific recombination mediated by the Cre recombinase results in the integration of the antibody plasmids at the chromosomal locus containing the lox sites and replacement of the eCFP and DsRed genes. Recombinants can then be isolated as blue-negative, red-negative, and green-positive cells by flow cytometry. Accordingly, CHO cells transfected with recombinant plasmids having a heavy chain variable region sequence and plasmids having a light chain variable region sequence from the same B cell were sorted by flow cytometry, and proper recombinants that show the blue-negative, red-negative, and green-positive phenotype were isolated, and stable recombinant antibody-expressing CHO cell lines were established from isolated clones.

Example 3. Antigen Binding Affinity Determination

The $K_D$ of the antigen binding to the selected antibodies described above were determined by surface kinetics on a real-time biosensor surface plasmon resonance assay (BIAcore™). More specifically, the affinity of the antibodies for human IL-6R was measured using a BIAcore® 2000 or BIAcore® 3000. The antibody was captured on an anti-mouse IgG surface and exposed to various concentrations of recombinant hIL-6R protein either in monomeric or dimeric form. Kinetic analysis using BIAevaluation™ software was performed to obtain the association and dissociation rate constants.

Binding affinities of the antibodies to hIL-6R were also measured for either hybridoma-conditioned media or purified proteins by plate-based competition immunoassay. The antibody proteins were purified using Protein G affinity chromatography from hybridoma cell conditioning medium that was bovine IgG-depleted (Invitrogen). For the competition ELISA, briefly, constant amounts of antibody at different levels were premixed with serial dilutions of antigen protein, hIL-6R-hFc, ranging from 0 to 10 µg/ml, and incubated for two hours at room temperature to reach pseudo-binding equilibrium between the antibody and antigen. These solutions were then transferred to 96-well hIL-6R-hFc pre-coated plates to allow the free-antibody in the mixtures to bind to plate-coated hIL-6R-hFc. The plates were typically coated with 1 to 2 µg/ml hIL-6R-hFc protein in PBS solution overnight at 4° C. followed by BSA nonspecific blocking. After washing off excess antibody in solution, plate-bound antibodies were detected with an HRP-conjugated goat anti-mouse IgG or IgA polyclonal antibody reagent and developed using either colorimetric or chemiluminescence substrates. The dependency of the signals on the concentrations of antigen in solution was analyzed with a 4-parameter fit analysis using Prism™ software (Graph Pad) and reported as $IC_{50}$. Competition immunoassays were also carried out using steady state solution phase Kinexa™ instrument (Sapidyne Inc.).

Results are shown in Table 1 (control: humanized monoclonal antibody to human IL-6R (U.S. Pat. No. 5,817,790 SEQ ID NO:69 and 71). Antibody (HCVR and LCVR amino acid sequences): VQ8A9-6 (3, 11); VQ8F11-21 (19, 27); VV7G4-1 (35, 43); VV7G4-10 (51, 59) VV6C10-1 (67, 75); VV6C10-3 (83, 91); VV6C10-4 (99, 107); VV6F12-11 (115, 123); VV9A6-11 (131, 139); VV6A9-5 (147, 155), VV3D8-4 (163, 171); VV1G4-7 (179, 187); 248982-13-1-E5 (195, 203); 248982-13-2-A9 (211, 219). Monomer and dimer $K_D$ determined by BIAcore™; solution $K_D$ by Kinexa™; $IC_{50}$ by ELISA assays (n.d.=not determined).

TABLE 1

| Antigen Binding Affinity | | | | |
|---|---|---|---|---|
| Antibody | $K_D$ Monomer (nM) | $K_D$ Dimer (nM) | Solution $K_D$ Monomer (nM) | ELISA $IC_{50}$ Dimer (nM) |
| VQ8A9-6 | 0.222 | 0.101 | 0.120 | 0.004 |
| VQ8F11-21 | 0.067 | 0.023 | 0.009 | 0.008 |
| VV3D8-4 | 2.410 | 0.172 | 1.910 | 0.013 |
| VV6A9-5 | 0.097 | 0.146 | 0.032 | 0.005 |
| VV1G4-7 | 0.225 | 0.070 | 0.197 | 0.041 |
| VV6C10-1 | 0.267 | 0.032 | 2.050 | 0.010 |
| VV6F12-11 | n.d | n.d | n.d | 0.033 |
| VV7G4-10 | n.d. | n.d. | n.d. | 1.980 |
| VV9A6-11 | n.d. | n.d. | n.d. | 0.347 |
| VV6C10-3 | n.d. | n.d. | n.d. | 0.009 |
| 248982-13-1-E5 | 0.987 | 0.785 | n.d. | 0.360 |
| 248982-13-2-A9 | 2.870 | n.d. | n.d. | 0.054 |
| Control | 1.790 | n.d. | 1.960 | n.d. |

Example 4. Neutralization of hIL-6 Activity hIL-6 blocking activities of the anti-hIL-6R antibodies of the invention were screened by hIL-6 blocking immunoassays, in vitro hIL-6 dependent cell growth bioassays, and surface plasmon resonance (BIAcore™). The immunoassay was used to screen ability of the tested antibody to block hIL-6 binding to hIL-6R, and the in vitro bioassay was used to determine the potency of the antibodies in neutralizing hIL-6R-mediated cellular signal transduction.

For the immunoassay, hIL-6 recombinant protein was coated on a 96-well plate in PBS buffer overnight at 4° C. This plate was used to capture free hIL-6R-hFc from antibody sample solutions, and the amount of captured hIL-6R-hFc was quantified according to the standard curve. The sample solutions were composed of a constant amount of hIL-6R-hFc recombinant protein (100 pM) and varying amounts of antibody, either in crude hybridoma condition medium or as purified antibody protein, ranging from 0 to about 50 nM in serial dilutions. The antibody-antigen mixtures were incubated at room temperature for ~2 hours to allow antibody-antigen binding to reach equilibrium. The equilibrated sample solutions were then transferred to the hIL-6 coated plates for measurement of free hIL-6R-hFc. After 1 hour binding, the plate was washed and bound hIL-6R-hFc was detected using HRP-conjugated goat anti-hFc polyclonal antibodies (Jackson Immuno Research), and developed using TMB substrate (BD Pharmigen). $IC_{50}$s were determined as the amount of antibody required to reduce 50% of IL-6R-hFc detectable to plate bound hIL-6 ligand. Results are shown in the first column of Table 2.

Additionally, the ability of the test antibody to block hIL-6 binding to the hIL-6R receptor was determined using surface plasmon resonance. Purified antigen hIL-6R-hFc molecules were captured by goat anti-human IgG polyclonal antibodies immobilized on CM-5 surface through amine coupling to a density of 250 RU. hIL-6 solution (0.25 ml, 50 nM) was injected over the receptor surface and bound hIL-6 recorded (first injection of IL-6). Bound hIL-6 was then removed with a pulse of 3 M $MgCl_2$ following by conditioning buffer. Anti-hIL6R antibody in hybridoma conditioned medium was injected over the captured receptor surface followed by second injection of hIL-6. The percent reduction in hL-6 binding resulting from preformed antibody and receptor complex was used as a score to define hIL-6 blockers from non-blockers (second column, Table 2).

TABLE 2

Neutralization of hIL-6 Binding

| Antibody | hIL6R/hIL6 Binding Inhibition $IC_{50}$ (nM) | hIL6/hIL6R Binding Inhibition (%) | XG-1 cell proliferation Inhibition $IC_{50}$ (nM) | HepG2/Stat3 Luciferase activity $IC_{50}$ (nM) |
|---|---|---|---|---|
| VQ8A9-6 | 0.39 | 68 | 0.40 | 0.097 |
| VQ8F11-21 | 0.12 | 98 | 0.62 | 0.135 |
| VV3D8-4 | 0.61 | 93 | >100 | n.d. |
| VV6A9-5 | 0.35 | 100 | 1.10 | 0.188 |
| VV1G4-7 | 1.10 | 34 | 1.80 | 0.578 |
| VV6C10-1 | 4.60 | 61 | >6.90 | n.d. |
| VV6F12-11 | 2.20 | n.d. | n.d. | n.d. |
| VV7G4-10 | 13.00 | n.d. | n.d. | n.d. |
| VV9A6-11 | 0.50 | n.d. | n.d. | n.d. |
| VV6C10-3 | 0.06 | n.d. | n.d. | n.d. |
| Control | 2.20 | 91 | 1.50 | 0.854 |

The ability of hIL-6R antibodies to block hIL-6 activity in vitro was measured in the hIL-6-dependent myeloma line XG-1. XG-1 cells maintained in hIL-6-containing medium were washed twice with hIL-6-free media and cultured for ~24 hours in hIL-6-free medium to deplete residual hIL-6. The starved cells were then spun down and re-suspended in the medium at $4 \times 10^5$ cells per ml and plated 20,000 cells per well in a 96-well tissue culture plate. The purified antibody proteins were serially diluted in medium and added to the plated cells at concentrations ranging from 0 to 50 nM. Subsequently, recombinant hIL-6 was added to the wells to a final concentration of 8 pM. Cells were allowed to grow for ~72 hours at 37° C. in a humidified 5% $CO_2$ incubator. At the end of growth period, live cells were measured using CCK-8 kit (Dojindo, Japan). $IC_{50}$s were determined as described above, and reported in the third column of Table 2.

The ability of hIL-6R antibodies to block hIL-6 activity was also measured in vitro in the hIL-6-responsive human hepatoma cell line, HepG2. HepG2 cells were transfected with a reporter plasmid containing a STAT3 (Signal Transducer and activator of Transcription 3) response element linked to a luciferase gene. The transfected cells were trypsinized, spun down and re-suspended in the medium at approximately $2.5 \times 10^5$ cells per ml and plated at 20,000 cells per well in a 96-well tissue culture plate. The purified antibody proteins were serially diluted in medium and added to the plated cells at concentrations ranging from 0 to 100 nM. Subsequently, recombinant hIL-6 was added to the wells to a final concentration of 50 pM. The response was measured after incubating the cells for 6 hours at 37° C. in a humidified 5% $CO_2$ incubator. Luciferase activity was measured with the Steady-Glo™ luciferase assay system (Promega). $IC_{50}$s were determined as described above, and reported in the fourth column of Table 2.

Example 5. Binding Epitope Diversity

An antibody binding competition immunoassay was performed using as a control humanized antibody to human IL-6R. Briefly, a 96-well immunosorbent plate was coated with 20 ng per well hIL-6R recombinant protein overnight at 4° C. After blocking non-specific binding with BSA, the hIL-6R binding sites on one half of the plate were saturated with binding of the control antibody by addition of 500 ng of the control per well, and to the other half of the plate was added binding buffer only. After three hours binding at room temperature, the purified antibodies were spiked in at a final concentration of 50 ng/ml with and without the preexisting control antibody in the well. After one hour of additional binding, the free antibody was washed away and the plate-bound antibody was detected with HRP-conjugated goat anti-mouse IgG or IgA, polyclonal antibody and the plate was developed using chromatic HRP substrates and absorbance at 450 nm was recorded. Percentage deductions of the binding of the anti-hIL6R antibodies by the presence of the control antibody are listed in Table 3 below. A similar experiment was conducted using surface plasmon resonance technology (Table 3). Both methods generated consistent results. Antibodies VQ8F11, VV3D8, VV6A9, and VV6C10-1 bound epitopes overlapping with the control antibody; while antibodies VQ8A9, VV1G4, VV6F12, VV7G4, VV9A6, and VV6C10-3 appeared to bind distinct epitopes as antigen binding was not blocked by the control antibody. Partial competition may result from steric hindrance from the first antibody bound, even though epitopes may not be overlapping.

TABLE 3

Competition of Antigen Binding with Control Antibody

| Antibody | BIAcore ™ (% reduction) | Immunoassay (% reduction) |
|---|---|---|
| VQ8A9-6 | 26 | 3 |
| VQ8F11-21 | 96 | 79 |
| VV3D8-4 | 97 | 84 |
| VV6A9-5 | 96 | 84 |
| VV1G4-7 | 12 | 3 |
| VV6C10-1 | 90 | 80 |

TABLE 3-continued

Competition of Antigen Binding with Control Antibody

| Antibody | BIAcore™ (% reduction) | Immunoassay (% reduction) |
|---|---|---|
| VV6F12-11 | n.d. | 3 |
| VV7G4-10 | n.d. | 26 |
| VV9A6-11 | n.d. | 18 |
| VV6C10-3 | n.d. | 1 |

Example 6. Cross-Species Binding Property

Four antibodies were tested for cross-reactivity to monkey IL-6R recombinant protein using BIAcore™ technology. Briefly, a biosensor chip on which goat anti-mouse Fc polyclonal antibody was immobilized was used to present anti-hIL-6R monoclonal antibodies to a density of about 75 RU. Recombinant human or monkey monomeric IL-6R protein (*Macaca fascicularis*, extracellular domain; SEQ ID NO:251), at a concentration range between 1.25-40 nM, was injected over the antibody surface. The binding of the receptor to the antibody and the dissociation of the bound complex were monitored in real-time. Both association rate constant (ka) and dissociate rate constant (kd) were obtained, and $K_D$ calculated (Table 4).

TABLE 4

Comparison of Binding Affinity to Human and Monkey IL-6R

| Antibody | Antigen | ka ($M^{-1}S^{-1}$) | kd ($S^{-1}$) | $K_D$ (nM) |
|---|---|---|---|---|
| Control | Human IL6R | 1.74E+05 | 1.67E−04 | 0.963 |
|  | Monkey IL6R | 1.44E+05 | 1.68E−04 | 1.170 |
| VQ8F11-21 | Human IL6R | 8.51E+05 | 4.38E−05 | 0.051 |
|  | monkey IL6R | 3.39E+05 | 4.86E−05 | 0.143 |
| VV1G4-7 | Human IL6R | 2.57E+05 | 6.18E−05 | 0.240 |
|  | monkey IL6R | no binding |  |  |
| VV6A9-5 | Human IL6R | 5.18E+05 | 8.41E−05 | 0.162 |
|  | monkey IL6R | 5.00E+05 | 7.70E−05 | 0.154 |
| VQ8A9-6 | Human IL6R | 7.32E+05 | 2.76E−04 | 0.377 |
|  | monkey IL6R | 7.31E+05 | 4.16E−04 | 0.569 |

Among the four tested antibodies, VQ8F11, VV6A9, and VQ8A9 strongly reacted to monkey receptor with KD values that differed by about 1.5- to about 3-fold from human receptor binding, respectively. VV1G4, which was not blocked by the control antibody (Table 3), showed no binding to monkey receptor despite strong binding to the human receptor with $K_D$ of 241 pM.

Example 7. Effect of Constant Region on Binding Affinity

The binding affinity to monomeric hIL-6R of four antibodies having mouse IgG, human IgG1 or human IgG4 (wild-type and modified) were determined using BIAcore™ as described above except a goat anti-human Fc polyclonal antibody surface was used to capture hIgG antibodies. Monomeric hIL-6R was injected at concentrations of 12.5, 6.25, 3.12, and 1.56 nM. The ability of the antibodies to neutralize hIL-6-dependent HepG2/STAT3 signal transduction was also determined in a luciferase assay (IC50). IC50s for different IgG isotypes were similar, suggesting no effect of isotype on antibody affinity for antigen.

TABLE 5

Comparison of IgG Isotypes

| Antibody | IgG | ka ($M^{-1}S^{-1}$) | kd ($S^{-1}$) | $K_D$ (nM) | $IC_{50}$ (nM) |
|---|---|---|---|---|---|
| VQ8F11-21 | hIgG1 | 6.22E+05 | 4.54E−05 | 0.073 | 0.150 |
|  | hIgG4 | 7.17E+05 | 5.22E−05 | 0.073 | 0.228 |
|  | mIgG2a | 7.86E+05 | 5.27E−05 | 0.067 | 0.135 |
|  | modhIgG4 | 8.81E+05 | 4.70 5−05 | 0.053 | 0.249 |
| VQ8A9-6 | hIgG1 | 1.09E+06 | 2.60E−04 | 0.238 | 0.130 |
|  | hIgG4 | 1.17E+06 | 2.35E−04 | 0.201 | 0.185 |
|  | mIgG1 | 9.95E+05 | 2.21E−04 | 0.222 | 0.097 |
| VV6A9-5 | hIgG1 | 7.12E+05 | 8.87E−05 | 0.125 | 0.204 |
|  | hIgG4 | 5.67E+05 | 7.64E−05 | 0.135 | 0.343 |
|  | mIgG2a | 7.72E+05 | 7.52E−05 | 0.097 | 0.188 |
| VQ1G4-21 | hIgG1 | 3.34E+05 | 7.92E−05 | 0.237 | 0.767 |
|  | hIgG4 | 2.73E+05 | 9.18E−05 | 0.336 | 0.528 |
|  | mIgG2a | 3.41E+05 | 7.66E−05 | 0.225 | 0.578 |

The invention claimed is:

1. An isolated nucleic acid molecule encoding an antibody or antibody fragment which specifically binds human interleukin-6 receptor (hIL-6R), wherein the antibody or antibody fragment comprises:
   three heavy chain complementarity determining region (CDR) sequences; and
   three light chain CDR sequences;
   wherein the three heavy chain CDR sequences are SEQ ID NO:181, 183 and 185; and
   wherein the three light chain CDR sequences are SEQ ID NO:189, 191 and 193.

2. The nucleic acid molecule of claim 1, wherein the antibody or antibody fragment comprises a heavy chain variable region (HCVR) comprising the amino acid sequence of SEQ ID NO:179.

3. The nucleic acid molecule of claim 1, wherein the antibody or antibody fragment comprises a light chain variable region (LCVR) comprising the amino acid sequence of SEQ ID NO:187.

4. A recombinant expression vector comprising the nucleic acid molecule of claim 1.

5. An isolated host cell comprising the expression vector of claim 4.

6. The host cell of claim 5 being a prokaryotic cell or an eukaryotic cell.

7. The host cell of claim 5, wherein the prokaryotic cell is an *E. coli* cell and the eukaryotic cell is a CHO cell.

8. A method of producing an antibody or antibody fragment which specifically binds human interleukin-6 receptor (hIL-6R), comprising growing the host cell of claim 5 under conditions permitting production of the antibody or fragment thereof, and recovering the antibody or fragment thereof so produced.

9. An isolated nucleic acid molecule encoding an antibody or antibody fragment which specifically binds human interleukin-6 receptor (hIL-6R), wherein the antibody or antibody fragment comprises a heavy chain variable region and light chain variable region pair (HCVR/LCVR) SEQ ID NO:179/187.

10. The nucleic molecule of claim 9, wherein the HCVR/LCVR pair is encoded by a nucleotide sequence pair of SEQ ID NO: 178/186.

11. A recombinant expression vector comprising the nucleic acid molecule of claim 9.

12. An isolated host cell comprising the expression vector of claim 11.

13. The host cell of claim 12 being a prokaryotic cell or a eukaryotic cell.

14. The host cell of claim 13, wherein the prokaryotic cell is an *E. coli* cell and the eukaryotic cell is a CHO cell.

15. A method of producing an antibody or antibody fragment which specifically binds human interleukin-6 receptor (hIL-6R), comprising growing the host cell of claim 12 under conditions permitting production of the antibody or fragment thereof, and recovering the antibody or fragment thereof so produced.

* * * * *